(12) United States Patent
Watanabe et al.

(10) Patent No.: US 11,413,191 B2
(45) Date of Patent: Aug. 16, 2022

(54) APPARATUS FOR PERFORATION AND ASPIRATION OF INNER EAR

(71) Applicant: THE TRUSTEES OF COLUMBIA UNIVERSITY IN THE CITY OF NEW YORK, New York, NY (US)

(72) Inventors: Hirobumi Watanabe, New York, NY (US); Anil K. Lalwani, Scarsdale, NY (US); James P. Stevens, New York, NY (US); Jeffrey W. Kysar, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 290 days.

(21) Appl. No.: 15/391,385

(22) Filed: Dec. 27, 2016

(65) Prior Publication Data

US 2017/0172804 A1 Jun. 22, 2017

Related U.S. Application Data

(63) Continuation of application No. PCT/US2015/038390, filed on Jun. 29, 2015.

(60) Provisional application No. 62/151,901, filed on Apr. 23, 2015, provisional application No. 62/052,091, filed on Sep. 18, 2014, provisional application No. 62/018,033, filed on Jun. 27, 2014.

(51) Int. Cl.
*A61F 11/20* (2022.01)
*A61B 17/3205* (2006.01)
*A61B 10/00* (2006.01)
*A61N 1/05* (2006.01)
*A61B 17/00* (2006.01)

(52) U.S. Cl.
CPC ........ *A61F 11/202* (2022.01); *A61B 10/0045* (2013.01); *A61B 17/32053* (2013.01); *A61N 1/0541* (2013.01); *A61B 2010/0054* (2013.01); *A61B 2017/00867* (2013.01); *A61B 2217/005* (2013.01)

(58) Field of Classification Search
CPC ...... A61B 17/32053; A61B 2010/0054; A61B 10/0045; A61F 11/002
See application file for complete search history.

(56) References Cited

U.S. PATENT DOCUMENTS 3,990,453 A * 11/1976 Douvas ............... A61F 9/00763
606/107
4,832,045 A * 5/1989 Goldberger ........ A61B 10/0233
600/567
5,423,330 A * 6/1995 Lee .................... A61B 10/0233
600/566
5,782,852 A * 7/1998 Foggia ............. A61B 5/150022
606/182

(Continued)

OTHER PUBLICATIONS

K. Dandekar, et al., "3-D Finite-Element Models of Human and Monkey Fingertips to Investigate the Mechanics of Tactile Sense", Transactions of the ASME, vol. 125, Oct. 2003.

(Continued)

*Primary Examiner* — Alexander J Orkin
(74) *Attorney, Agent, or Firm* — Reed Smith LLP; Lisa A. Chiarini; Walter M. Egbert, III

(57) ABSTRACT

An apparatus for controlled perforation and aspiration of the inner ear.

23 Claims, 20 Drawing Sheets

(56) References Cited

U.S. PATENT DOCUMENTS

| | | | | | |
|---|---|---|---|---|---|
| 5,980,545 | A * | 11/1999 | Pacala | A61B 17/32002 | 606/170 |
| 6,193,129 | B1 * | 2/2001 | Bittner | A61B 17/1114 | 227/180.1 |
| 6,395,002 | B1 * | 5/2002 | Ellman | A61B 18/1485 | 606/45 |
| 6,610,235 | B1 * | 8/2003 | Lebouitz | A61B 5/150984 | 264/221 |
| 2002/0052619 | A1 * | 5/2002 | Transue | A61B 17/32053 | 606/185 |
| 2003/0069595 | A1 * | 4/2003 | Phung | A61B 17/32053 | 606/184 |
| 2004/0181185 | A1 * | 9/2004 | Lee | A61B 17/320016 | 604/6.16 |
| 2005/0149088 | A1 * | 7/2005 | Fukuda | A61B 5/150503 | 606/181 |
| 2005/0171567 | A1 * | 8/2005 | DeHart | A61B 5/150396 | 606/181 |
| 2005/0222598 | A1 * | 10/2005 | Ho | A61B 17/32056 | 606/171 |
| 2005/0245952 | A1 * | 11/2005 | Feller | A61B 17/32053 | 606/170 |
| 2006/0135917 | A1 * | 6/2006 | Reihl | A61B 5/14528 | 604/272 |
| 2007/0156164 | A1 * | 7/2007 | Cole | A61B 17/3468 | 606/187 |
| 2007/0244490 | A1 * | 10/2007 | Moehle | A61B 17/282 | 606/108 |
| 2008/0234602 | A1 * | 9/2008 | Oostman | A61F 2/10 | 600/564 |
| 2009/0156920 | A1 * | 6/2009 | Kotzan | A61B 5/14532 | 600/347 |
| 2009/0312692 | A1 * | 12/2009 | Cotter | A61B 17/320068 | 604/22 |
| 2011/0313429 | A1 * | 12/2011 | Anderson | A61B 10/0233 | 606/131 |
| 2013/0197395 | A1 * | 8/2013 | Janssens | A61B 10/0266 | 600/567 |
| 2015/0359556 | A1 * | 12/2015 | Vardi | A61B 17/32053 | 606/170 |

OTHER PUBLICATIONS

"Human Engineering Design Data Digest", Department of Defense Human Factors Engineering Technical Advisory Group, Apr. 2000.

* cited by examiner

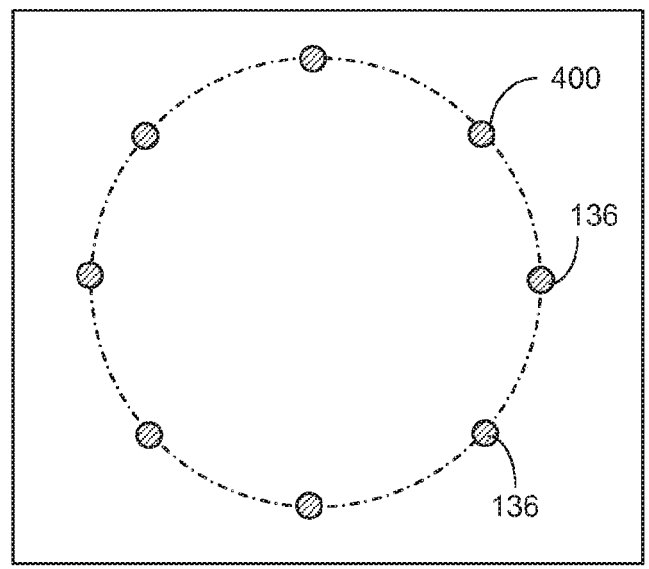
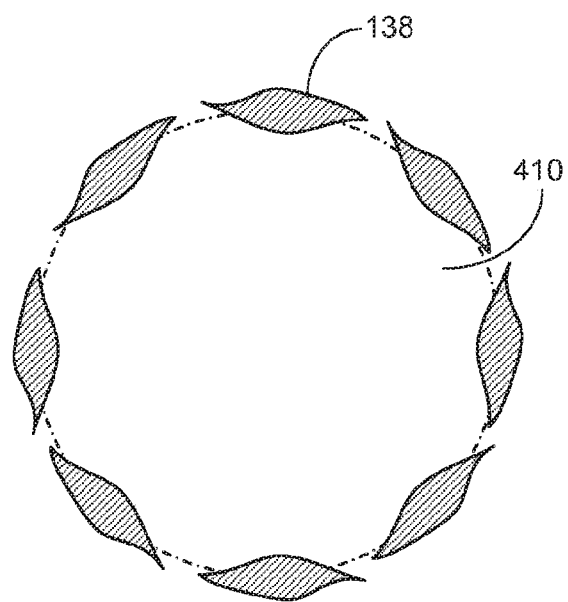
FIG. 4

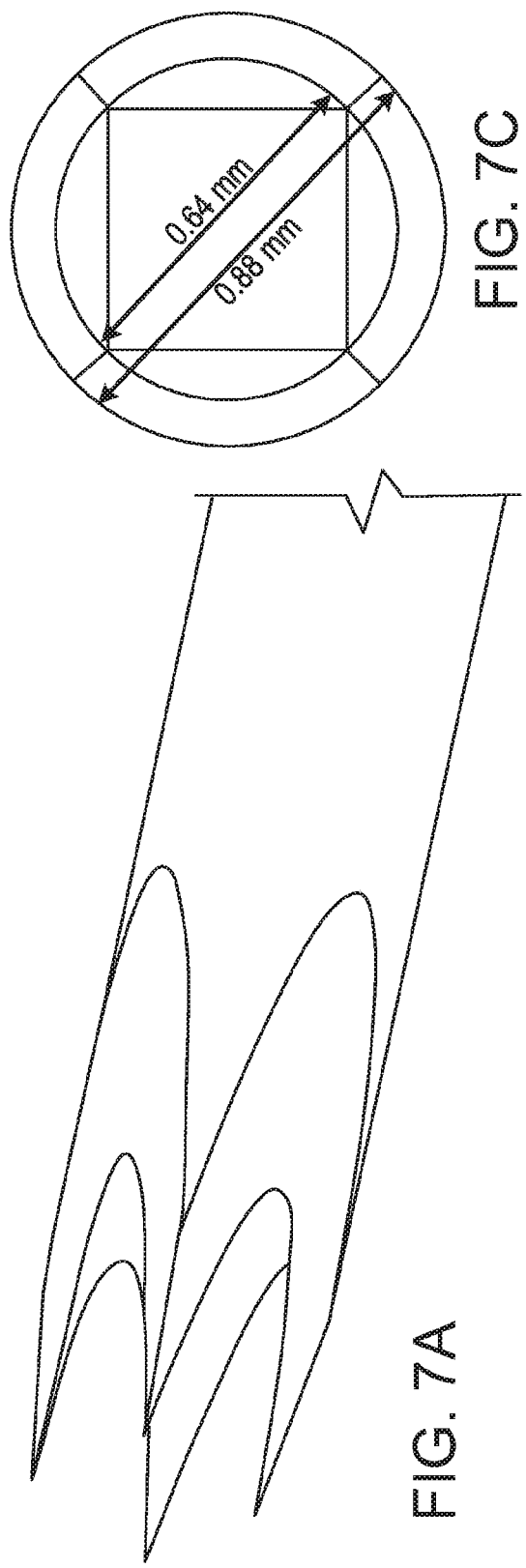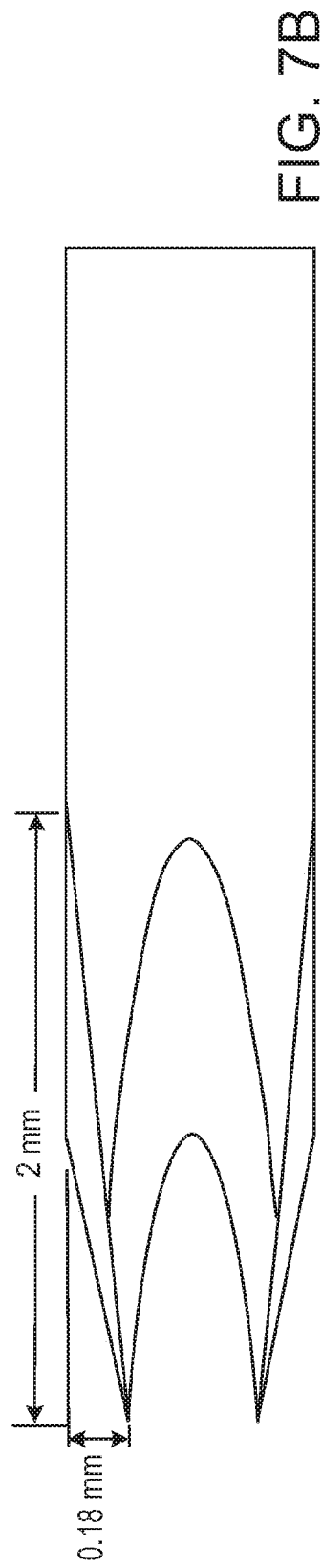

LONGITUDINAL PLANE VIIEW

500 μm

FRONTAL PLANE VIEW

APPARATUS FOR PERFORATION AND ASPIRATION OF INNER EAR

CROSS-REFERENCE TO RELATED APPLICATIONS

This application is a continuation of International Application No. PCT/US15/38390, filed Jun. 29, 2015, which claims the benefit of U.S. Provisional Application No. 62/018,033, filed Sep. 18, 2014, U.S. Provisional Application No. 62/052,091, filed Jun. 27, 2014, and U.S. Provisional Application 62/151,901, filed Apr. 23, 2015 the contents of each are hereby incorporated by reference in their entirety.

TECHNICAL FIELD

The disclosed subject matter describes an apparatus having controlled precision for perforating a thin membrane in the ear. More particularly, the subject matter described is a punch device configured to produce a controlled and precisely shaped and sized perforation in a thin membrane of an inner ear. An additional aspect of the disclosure is an apparatus for aspirating perilymph fluid from within the inner ear.

BACKGROUND

The inner ear is a common site of pathology that can have debilitating effects on one's quality of life. Symptoms such as hearing loss, tinnitus, and vertigo are quite prevalent in the general population, and are frequently the cause of a patient's presentation to the physician. These symptoms, either alone or in combination with one another, can be reflective of underlying otologic disorders that necessitate specific medical or surgical intervention. Despite previous research and innovation, effective treatments for inner ear illnesses such as sudden sensorineural hearing loss (SSNHL) and Meniere's disease have remained particularly elusive. A major reason for the inability to precisely diagnose a patient is the current inability to perform specific diagnostics within the inner ear. This is due to the anatomic inaccessibility of the cochlea. As a consequence the physician is often not able to determine the specific etiology of a patient's presentation, and thus is unable to target treatments for the individual cause. For example, over 70% of SSNHL cases remain idiopathic, while Meniere's disease is a clinical diagnosis of exclusion that typically takes 3-5 years of expensive testing and a worsening, often-permanent clinical presentation to reach. The treatments for these and similar diseases, meanwhile, are typically non-specific intratympanic steroids or ototoxic antibiotics because the exact cause remains unidentified. However, treatment with these drugs provide unproven efficacy in meta-analyses, and can harm the patient's current cochlear functioning.

Within the cochlea, the scala tympani and scala vestibuli are filled with a solution of fluid called perilymph. This solution is critical to the transduction of air vibrations into neural signals via the hair cells. When a patient has an acute or chronic illness of inner ear etiology, it is highly likely to be reflected by abnormalities in the chemical make-up of the perilymph, such as changes in the presence or concentration of various ions, proteins, bacteria, or viruses. Previous intra-operative studies on perilymph collection during cochlear implantation or tumor resection have allowed clinicians to differentiate disease etiology. During cochlear implantation surgery, an incision is created in the interface between the inner and middle ears, such as the RWM to allow insertion of a tubular cochlear implant. In animal studies, methods of perilymph sampling have often utilized the creation of a basal or apical cochleostomy, requiring disruptive surgical drilling of the cochlear wall and putting the patient at risk for hearing loss.

The RWM and the oval window are entrances into the scalae and thus provide a promising portal for fluid aspiration of perilymph. Currently, clinicians employ devices and techniques developed for other purposes to enter the inner ear. A hypodermic needle is typically used to create an incision in the round window membrane or a myringotomy knife is used to create a slit or cruciform to make an opening large enough to insert an implant for both tympanostomy and cochlear implant. These methods create either a smaller hole (so that a cochlear implant insertion results in expanding the hole in the compliant membrane), or a larger hole (so that the leak is present or is closed somehow.) Traumatic perforation inhibits effective membrane healing, and also contaminates perilymph samples with tissue fluid, blood, and cerebrospinal fluid (CSF) as perilymph is lost to the middle ear.

Hypodermic needles typically have a beveled tip to reduce the force required to penetrate the tissue of a patient. During the penetration of a thin membrane with a hypodermic needle, the tip of the needle pushes the membrane causing the deflection until the tip causes a rupture of the membrane. The force applied to the membrane drops at the moment of the membrane rupture. Pushing the needle further into the membrane again requires increase of the force to create the hole and to push against friction until the shaft of the needle is in the membrane. During the course of this penetration process, the flexible membrane undergoes significant deformation. The diameter of the hole left in the membrane is a result of plastic deformation and release of pretension of the membrane without any loss of the tissue. Therefore the diameter of the hole will not become the diameter of the needle and can't be controlled well.

Therefore, there is a need for an apparatus that can create a precise, circular perforation in a thin membrane, aspirate perilymph from the inner ear without causing traumatic perforation of the membranes, as well as an apparatus useful for efficient and specific diagnoses of inner ear problems to allow for more personalized and targeted inner ear therapy.

SUMMARY

The present disclosure provides enabled teachings of an apparatus and method for the atraumatic, precise perforation of a thin membrane and sampling fluid in the inner ear. The apparatus and methods for perforation and aspiration of the inner ear described in this disclosure open the door for clinicians to individualize inner ear diagnosis and treatment. Effective fluid analysis of the perilymph through various techniques, including liquid chromatography-tandem mass spectrometry (LC-MS/MS) can provide personalized and accurate diagnostics. Such analysis comes at a time when the amount of data describing gene expression and proteomics is rapidly growing.

In one aspect, an apparatus designed for easy access to the thin membrane of the inner ear via an ear canal and middle ear space is provided. The apparatus perforates the thin membrane with minimal damage. In one embodiment, the apparatus comprises a hollow tubular member having a proximal portion and a distal portion and a length therebetween. The distal portion includes a plurality of alternating apices and valleys forming serrated blades for precise circular perforation of a thin membrane of the inner ear, such as the round window membrane and tympanic membrane. The polyhedral configuration can be one or more wedge configurations, a pyramidal configuration, or other like configurations.

In another aspect, the apparatus is an aspiration device capable of aspirating inner ear fluid precisely and efficiently. In this aspect, the tubular member may further include a proximal end adapted for connection to a vacuum or other suction means. In another embodiment, the tubular may include an aspirating force within its hollow tubular member. In some embodiments the lumen formed by the hollow tubular member, at least at its distal end, may include a chamber, such as a small distal volume of the lumen. A pulse of negative pressure can be developed within the small volume inside the lumen to create an aspirating force.

In some embodiments, the apparatus includes a handle. The handle may have a curved tip made of medical grade stainless steel, whose dimensions are suitable for the anatomy of the ear. The apparatus may further a stopper disposed proximal the distal portion of the tubular member.

In another aspect, a method for manufacturing the apparatus is provided.

BRIEF DESCRIPTION OF THE DRAWINGS

A detailed description of various aspects, features and embodiments of the subject matter described herein is provide with reference to the accompanying drawings, which are briefly described below. The drawings are illustrative and are not necessarily drawn to scale, with some components being exaggerated for clarity. The drawings illustrate various aspects and features of the present subject matter and may illustrate one or more embodiment(s) or example(s) of the present subject matter in whole or in part. Together with the description, the drawings serve to explain the principles of the disclosed subject matter.

FIG. 4 is a depiction of crack propagation of a thin membrane caused by operation of an apparatus in accordance with an exemplary embodiment of the tubular member.

FIG. 7A-C are perspective, side and cross sectional views, respectively, of an exemplary embodiment of tubular member having four tips or serrated edges at the distal tip.

DESCRIPTION OF THE DISCLOSED SUBJECT MATTER

The disclosed subject matter is directed to an apparatus that enables the easy and precise perforation of tympanic or round window membranes of the inner ear of a subject to accommodate an implant, such as cochlear implant, or to aspirate fluid from the inner ear. The apparatus may also be used for tympanostomy. In addition, methods of manufacturing and using the apparatus are described.

Figure 1:
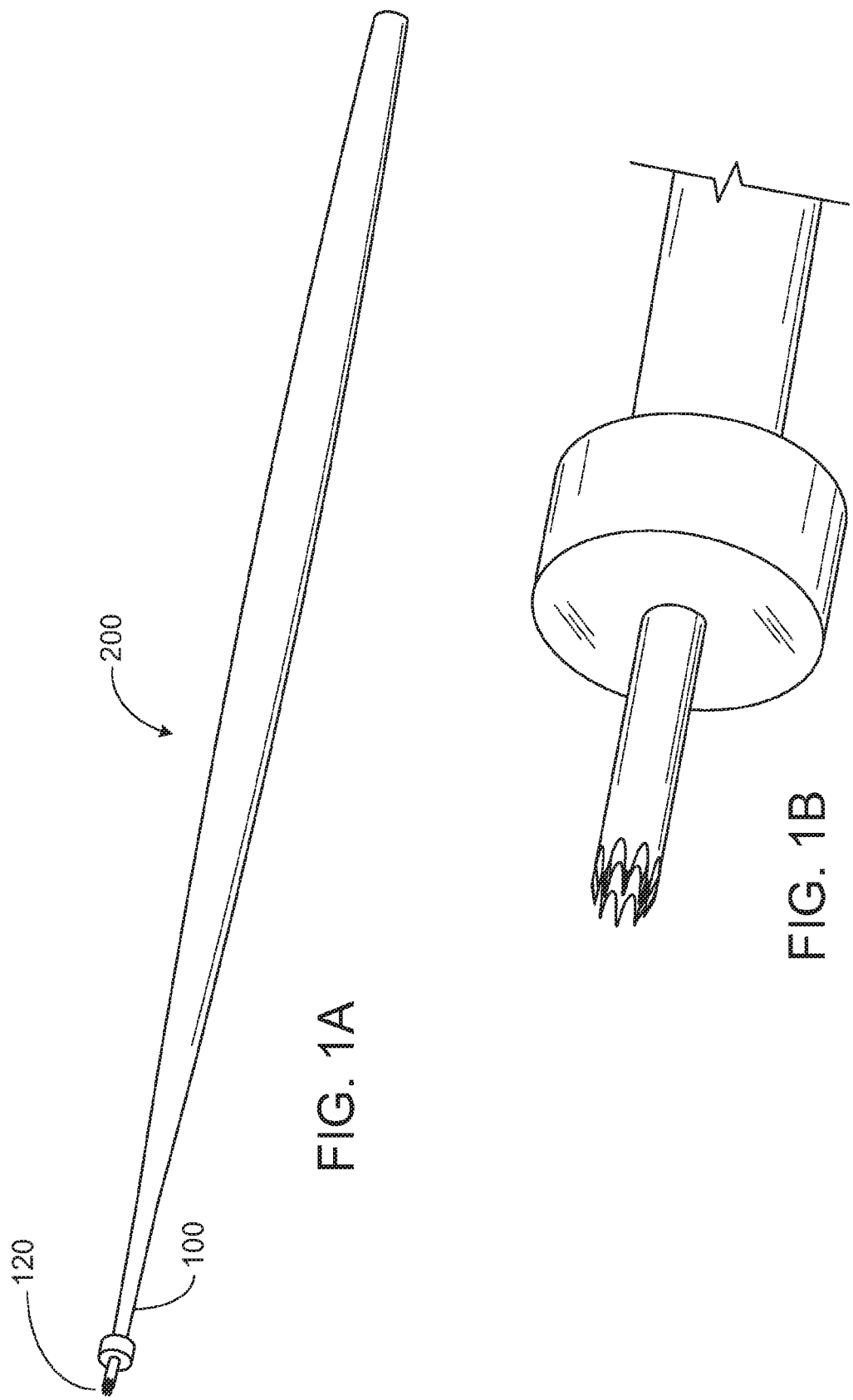
FIGS. 1A and 1B are perspective views of an apparatus in accordance with an exemplary embodiment of the disclosed subject matter.
Figure 2:
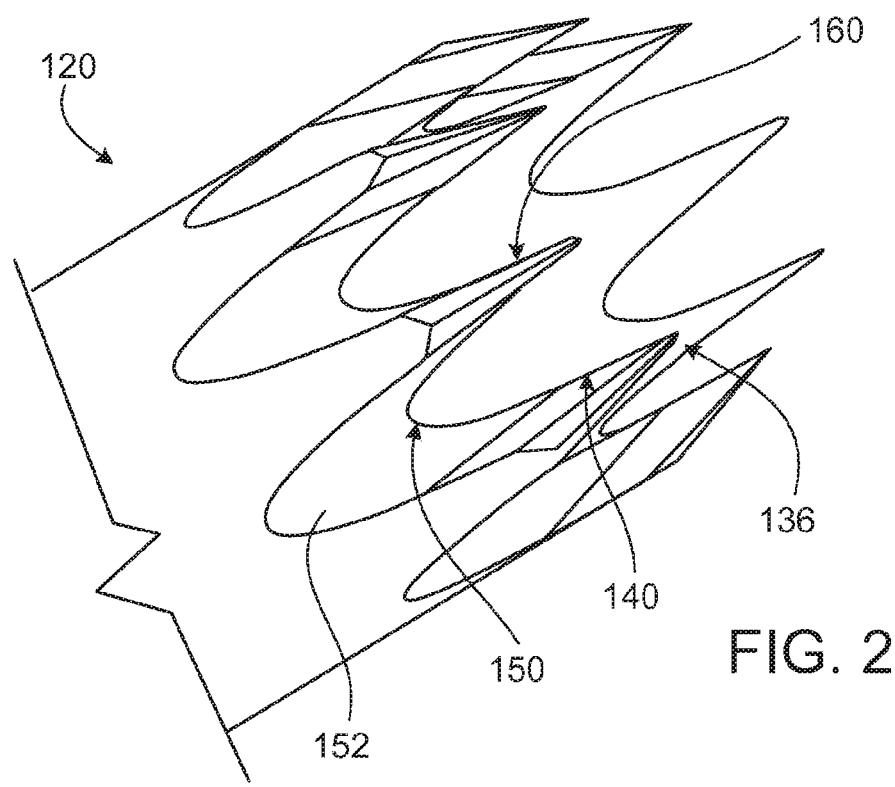
FIG. 2 is a perspective view of the distal section of the tubular member, in accordance with an exemplary embodiment of the disclosed subject matter.

In accordance with one aspect, an apparatus is described for making a perforation in a thin membrane of the inner ear such that the perforation has an optimal shape and size to accommodate a permanent or semi-permanent implant with minimal physical consequences to the inner ear. With respect to this aspect, FIG. 1 generally depicts an apparatus comprising a tubular member 100 engaged to the distal end of handle 200. The tubular member 100 comprises a proximal portion 110 and distal portion 120. The proximal portion 110 is secured to handle 200. As best seen in FIG. 2, the distal portion 120 includes a plurality of alternating apices 130 and valleys 150, which form a serrated blade at the distal end of the tubular member.

Figure 5:
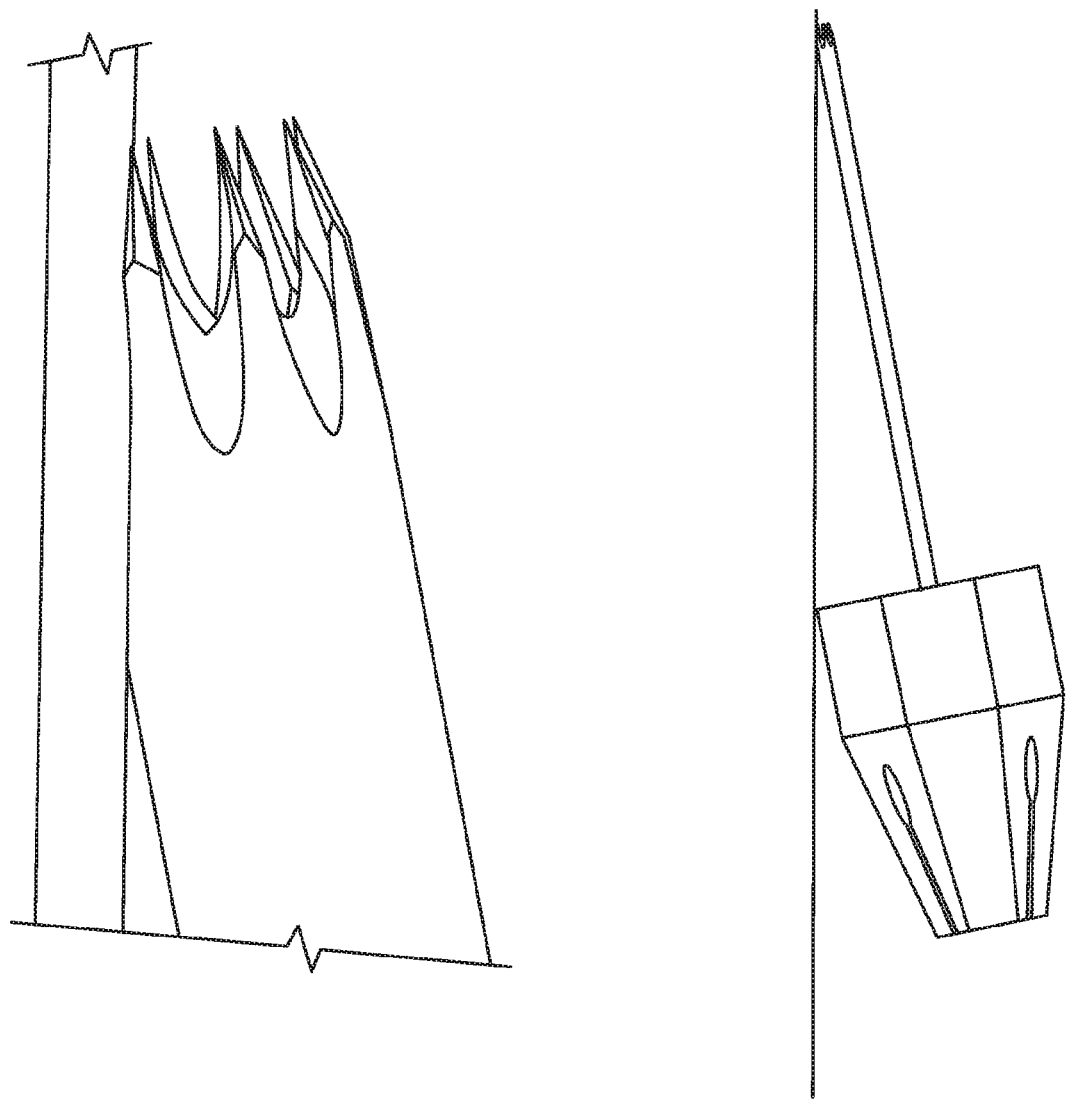
FIG. 5 illustrates a collet chuck to fix an ultra-thin metallic tubular member at a bevel angle against a wire of a wire electron discharge machine, in accordance with an exemplary embodiment of the disclosed subject matter.

In the embodiment depicted in FIG. 2, the apices 130 include pointed tip at the most distal end 136 and a trailing edge 140 extending proximally from the tip of the apex to the valley 150 forming a cutting blade. The valleys 150 include an arcuate edged surface 152 disposed between pairs of apices 130. The apices 130 and the valleys 150 formed by the inner surface of the distal portion of the tubular member 120 constitute a continuous arris, or ridge formed by the meeting of the two surfaces at an exterior angle, functioning as cutting edges. In one embodiment, the plurality of alternating apices 130 and valleys 150 form a plurality, e.g., eight, octagonal serrated blades 160. The tip and the trailing edge may be configured in a sharp slender needle, which enables penetration of a membrane with minimal force. The arcuate bottom edge can be beveled sharply against the inner cylinder of the needle such that the membrane is readily cut along the line of the circle of tube needle, as shown in FIG. 5. The arris of the tip to the bottom edge serration is configured to maintain the sharp edge against the membrane to cut it efficiently. Thus, the distal portion of the tubular member in some embodiments has a crown shaped configuration.

Figure 21:
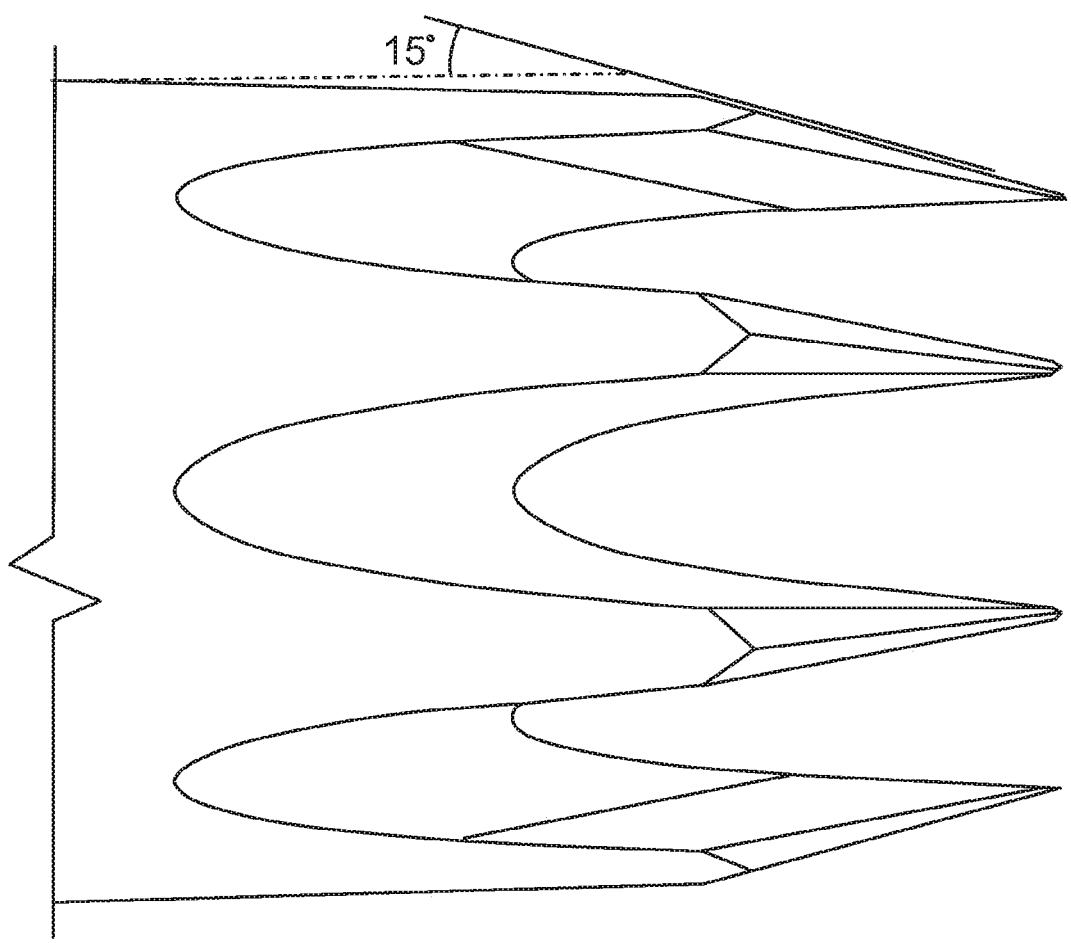
FIG. 21 is a side view of one embodiment of the tubular member illustrating a bevel angle of 15 degrees formed by the apices in accordance with an exemplary embodiment of the tubular member.

As shown in FIG. 21, in some embodiments, the tubular member 100 may include a bevel angle of 15 degrees formed by the apices 120 and longitudinal length of the tubular member.

Figure 3:
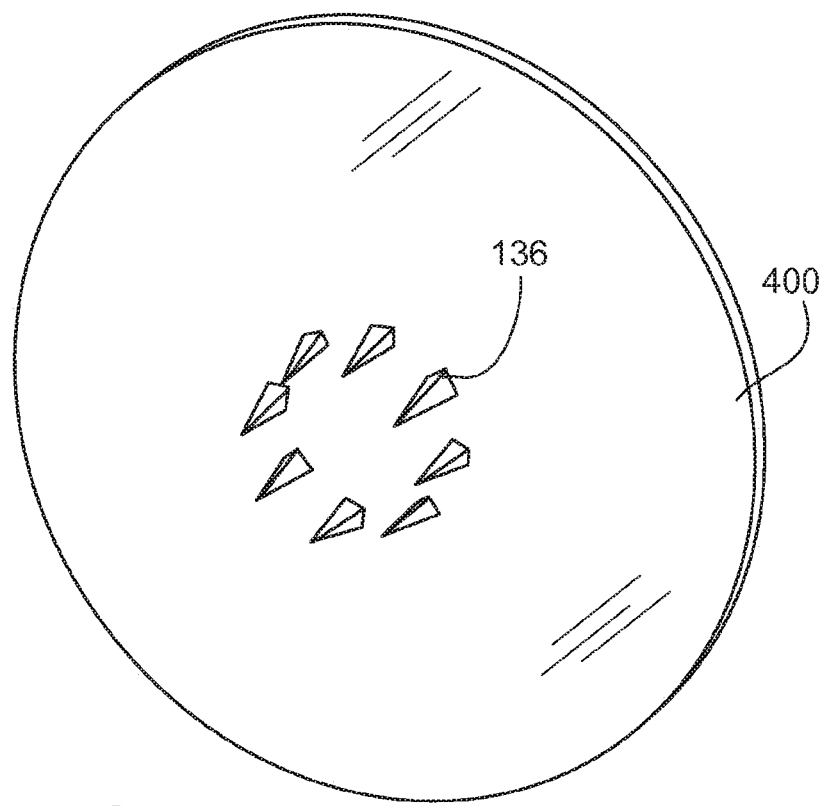
FIG. 3 is a bottom view of the tips of an apparatus of the present disclosure penetrating a thin membrane.

As seen in FIG. 3, the tips 136 of the apices penetrate the thin membrane 400 with minimal force application so that the deformation of the membrane can be minimized. As schematically shown in FIG. 4, after penetration of the thin membrane 400 by tips 136, the blades perforate 138 the thin membrane and a portion of the membrane is circumferentially disposed within the tubular member and held in place by the plurality of apices. The thin membrane 410 is isolated from deformation of the membrane. As the distal end of the apparatus is pushed deeper inside of the membrane by increasing the force, the arris of the blades cuts the membrane along the circular trace of the inner surface of the needle. Finally, as the arcuate bottom edges of the blades separates the membrane 410 inside apparatus from the remainder of the membrane 400, a hole which approximates the cross section of the inner circle of the apparatus is left in the inner ear. The portion of the membrane, e.g., RWM, that is severed by the serrated edges of the apparatus can be captured and retained within a lumen of the tubular member. In other embodiments, depending on the tip configuration, only a portion of the RWM is severed to form a flap which maintains continuity with the remainder of the RWM via the unsevered portion. In other words, the cutting line does not circumscribe or extend completely around the needle tip.

During this perforation, the membrane undergoes significant deformation and deflection. However, the deformation within the region inside apparatus distal end will be minimized because the inside region will be pinned by the tips throughout the process. Therefore, the size and the shape of the hole will be well-controlled predominantly by the apparatus shape independent of the variability of the physical properties of the membrane of the individual patients as well as the technical variation of individual physicians.

In one embodiment, the tubular member 100 of the disclosed subject matter includes a stainless steel tube needle with ultra-thin wall, such as a hypodermic needle adapted with a plurality of alternating apices and valleys to form serrated blades extending distally from the tubular member. Although the exemplary embodiment refers to eight octagonally-aligned serrations, it is understood that needle may be fabricated with a fewer or greater number of serrations, typically ranging from two to ten, with some embodiments having a specific number, e.g., 3, 4, 5, 6, 7, 9, 10, 11, 12, while other embodiments may include even more serrations.

Figure 6:
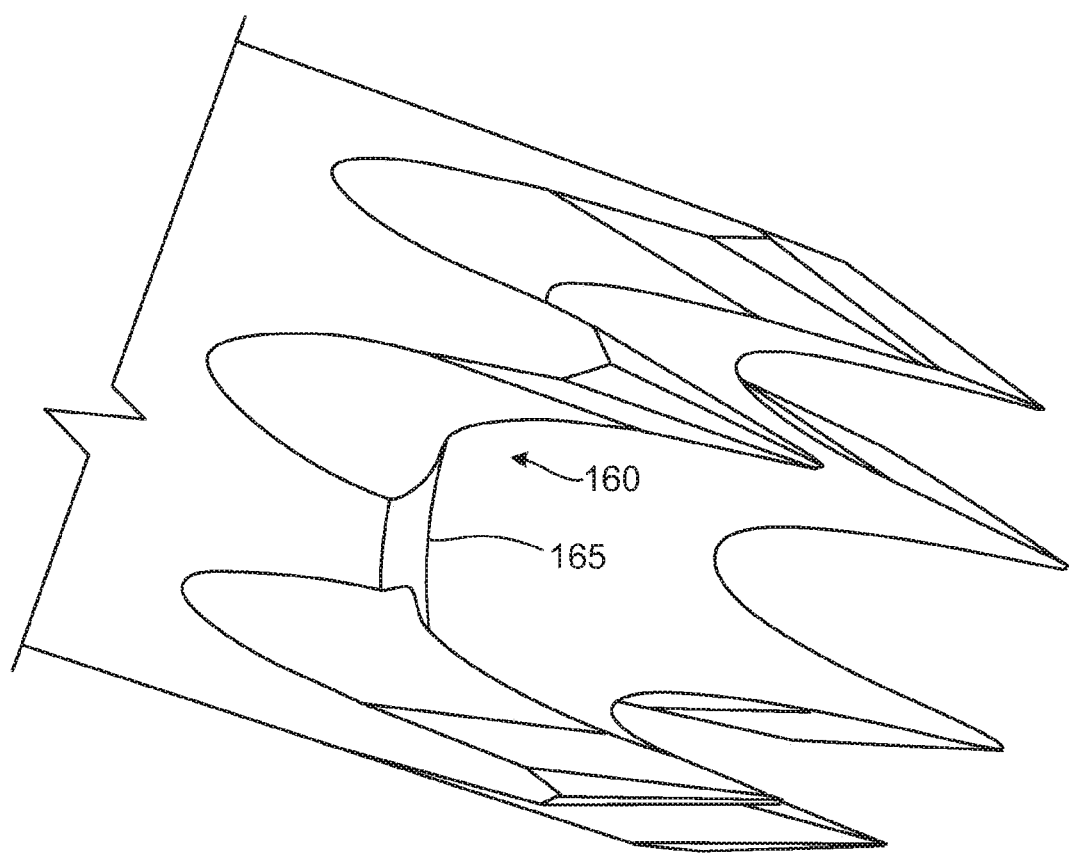
FIG. 6 is a side view, illustrating a bevel angle and the surface cut by a wire pass from three angle set by a collet chuck, i.e., one cut surface from a first angle and a second cut surface from another angle, in accordance with an exemplary embodiment of the disclosed subject matter.

In another embodiment, as shown in FIG. 6, one of the plurality of blades is removed and replaced with a slit 160 in order to prevent losing the separated membrane tissue into the middle/inner ear. In an exemplary embodiment, one of the sharp tips is removed via wire discharge machining, such that the octagonally-beveled needle is equipped with seven sharp points and one recessed wall 165. A membrane that is penetrated by the seven sharp points followed by the cut at the arcuate bottom edges will still be attached at the recessed portion of the membrane. This partial attachment prevents uncontrolled migration of the membrane into the inner ear space possibly causing unwanted complication in the inner ear.

Figure 22:
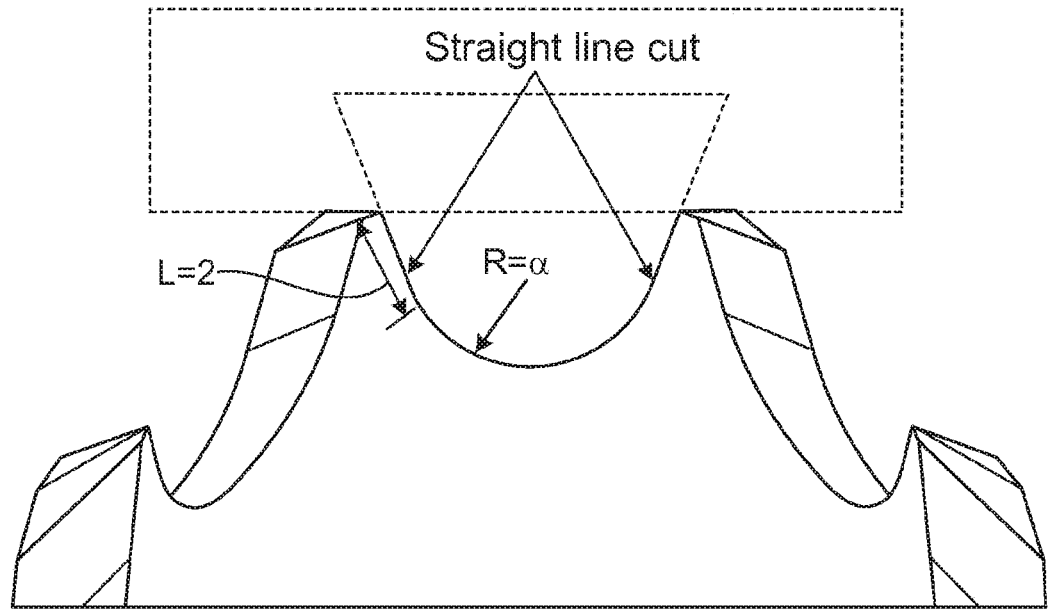
FIG. 22 is a view of the tubular member from the bevel angle of 15 degrees, illustrating wire electron discharge machine cut lines, from the angle depicted and faces from a second angle cut, including tip defined from two cut planes in accordance with an exemplary embodiment of the disclosed subject matter.
Figure 23:
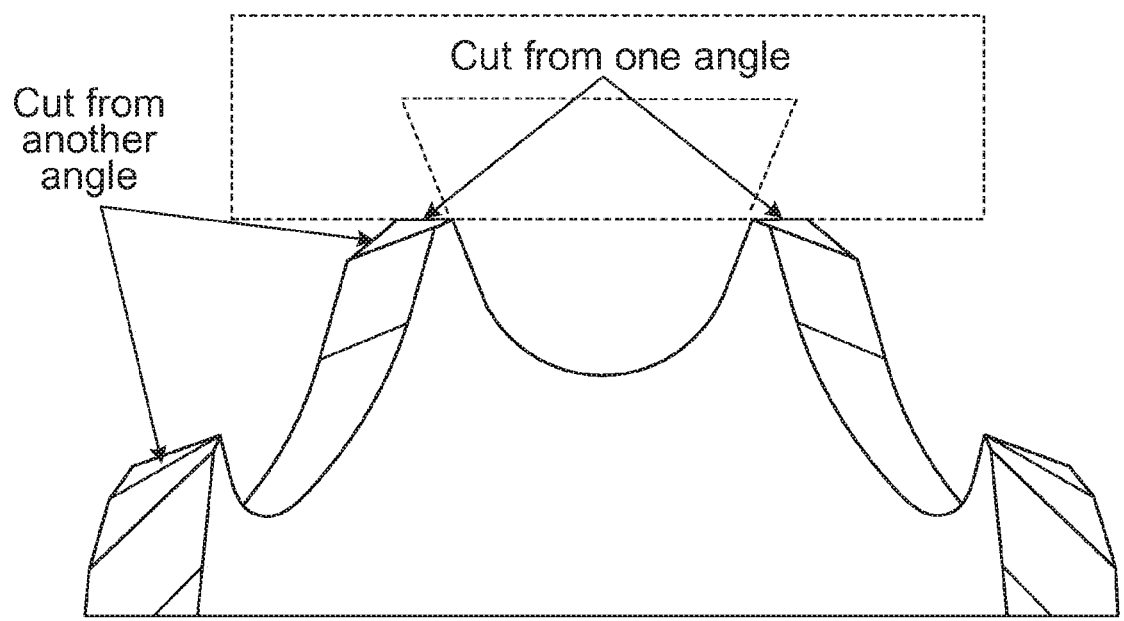
FIG. 23 is a top view, illustrating two cut surfaces from straight line cuts, i.e., one cut from a first angle and a second cut from another angle in accordance with an exemplary embodiment of the disclosed subject matter.
Figure 24A:
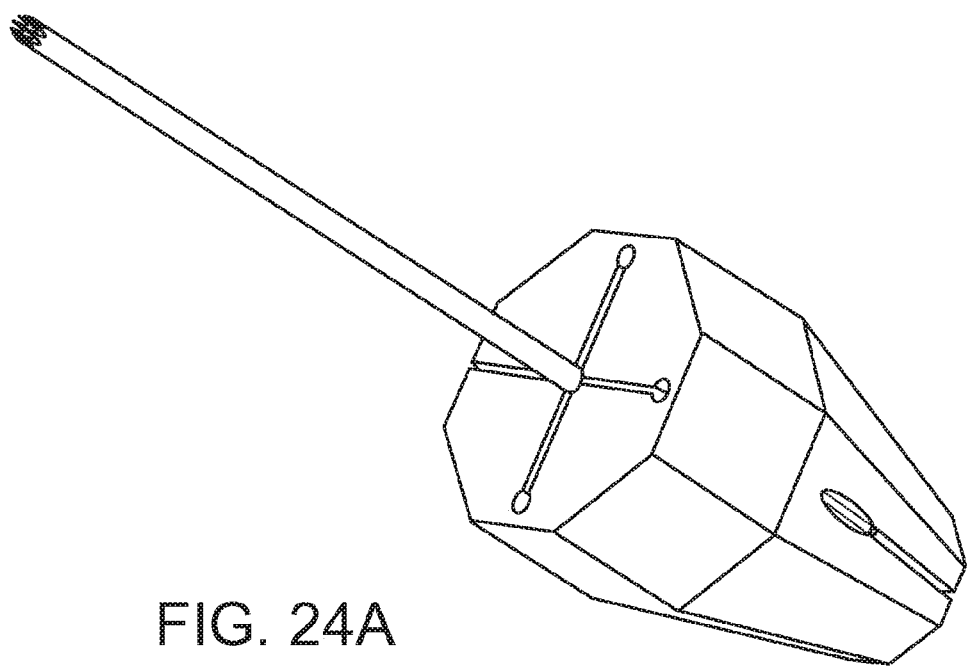
FIGS. 24A-D illustrate various perspectives of a bevel angle jig in accordance with a method of the disclosed subject matter.
Figure 24B:
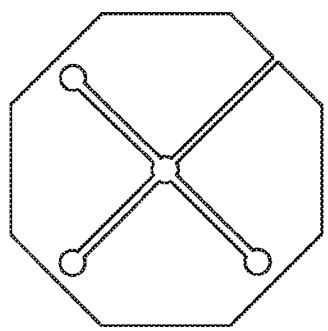
Figure 24C:
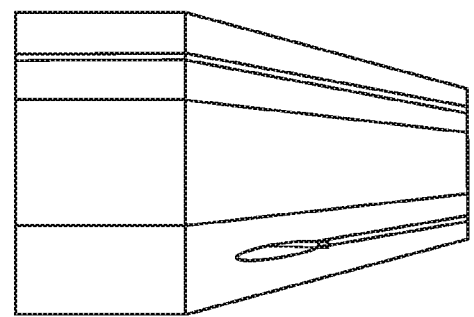
Figure 24D:
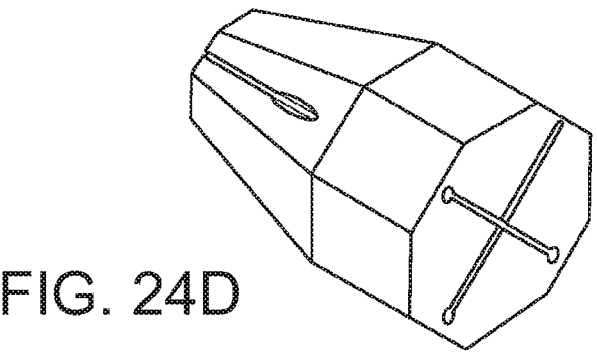

A manufacturing method via wire electron discharge machining of a tubular member having an outer diameter of about 0.8 to about 1.1 mm is also disclosed. In an exemplary embodiment, a tubular member, such as a stainless steel needle with ultra-wall, such as a hypodermic needle at 21 gauge (0.8 mm outer diameter with 0.089 mm thick), is beveled with a wire electron discharge machine. As seen in FIG. 22, the tubular member can have a bevel angle of 15 degrees, as shown, wire electron discharge machine cut lines can be made, from the angle depicted and faces from a second angle cut, including tip defined from two cut planes. Additionally, as depicted in FIG. 23 two cut surfaces from straight line cuts. i.e., one cut from a first angle and a second cut from another angle.

A needle is mounted in a collet chuck which has an octagonal cross section such that the needle can be rotate at 45 degree around the center line of the needle incrementally. FIGS. 24A-D illustrate various perspectives of a suitable collet chuck. And, each octagonal face has a slightly slanted face to rotate the needle at a designed bevel angle. Via wire electron discharge machine, the needle is cut with a wire in a trajectory which includes (1) two lines, (2) an arc and (3) two lines with a line symmetry in the middle that coincides with the centerline of the needle. In the exemplary embodiment, two of the lines cut the needle to create octagonal facets at a 15 degree bevel angle and the tip of the eight fingers. Another type of line cut creates a facet that makes the sharp-wedged-shaped trailing edge. The arc cut creates the arcuate bottom edges.

As depicted in the exemplary embodiment of FIGS. 7A-C, the beveled or serrated edges extend a distance of 2 mm from the distal tip of the needle. The apex or crown of the serrated tip is positioned 0.18 mm radially inward from the outer diameter of the needle, as shown in FIG. 7B. Additionally, the exemplary embodiment of the needle is configured with lumen extending throughout and having an inner diameter of 0.64 mm and an outer diameter of 0.88 mm, as shown in FIG. 7C.

In accordance with another aspect of the disclosure, the apparatus is configured to aspirate fluid from the inner ear, e.g., perilymph aspiration. In this aspect, the apparatus described above can be configured with an aspirator to aspirate fluid from the inner ear after penetration of the inner ear membranes. The aspirator, for example, can be a vacuum or aspirating force engaged to the proximal end of the apparatus, or alternatively, a vacuum or aspirating force can be caused within the lumen of the apparatus by creation of negative pressure.

Figure 8:
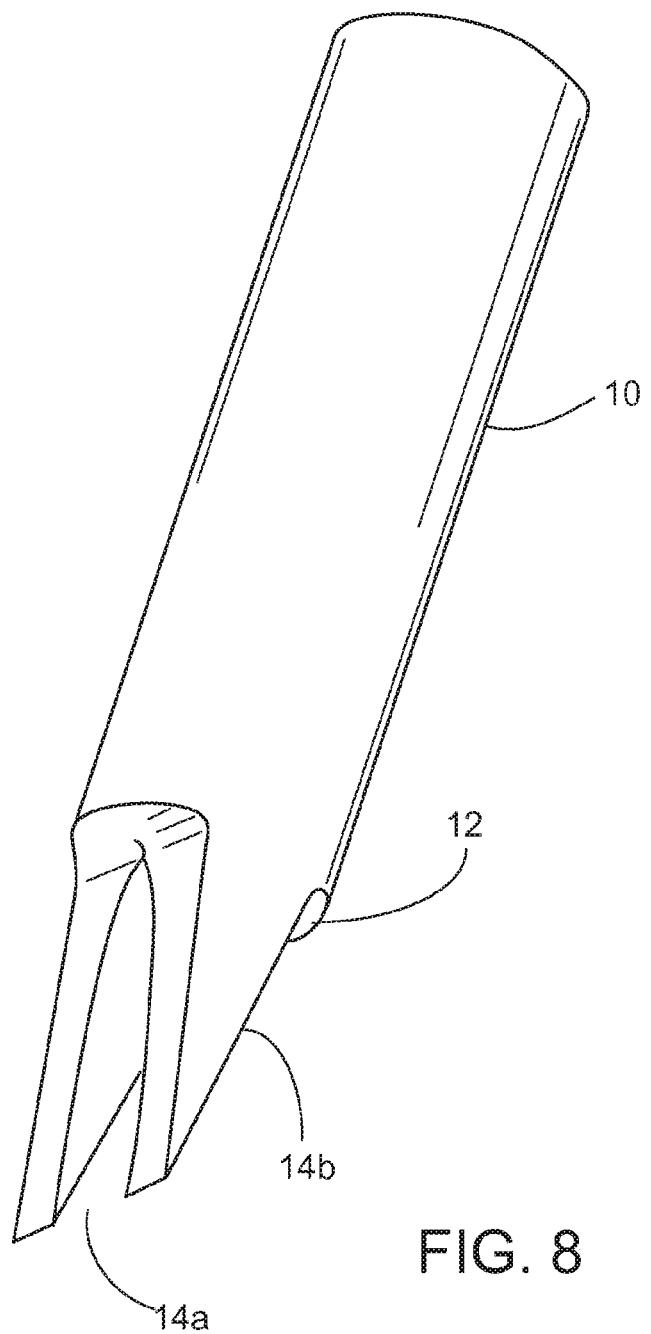
FIG. 8 is a schematic view of an exemplary embodiment of an aspiration apparatus having dual wedge tip

In another embodiment, an aspiration apparatus 10 is configured as a hollow dual-bladed tubular member, as depicted in FIG. 8. The apparatus 10 can both atraumatically perforate the human ear's RWM and subsequently aspirate samples of inner ear fluid, e.g., perilymph. The capability to sample perilymph from sufficient individuals can lead to the understanding of the presence or given concentration of a specific protein, ion, bacteria, or vial segment within the fluid which can be correlated to a patient's disease or risk factors. This information can lead to more personalized treatment plans, targeting the underlying etiology of each clinical presentation in a field that is currently wrought with ineffective treatments and ototoxic side effects.

For purposes of illustration and not limitation, an exemplary embodiment of the apparatus 10 can be formed from a 31 gauge needle having an outer diameter of 0.25 mm and an inner diameter of 0.1 mm at the proximal end 10, as shown in FIG. 8. The apparatus 10 can include a flange 12 disposed at the intersection of the proximal portion of the needle 10 and the base of the tip 14 having a first and second wedge shaped configuration forming dual-needles 14a,14b. The flange 12 can be formed with an outer diameter equal to the outer diameter of proximal portion 10, as shown. In some embodiments, the flange 12 can be configured with a greater outer diameter so as to protrude or extend radially outward from the proximal portion of the needle 10. The flange 12 can be formed having a flat or planar surface at the distal, or axial, end thereof. The frictional forces generated between the flange 12 and the RWM upon operation of the apparatus grabs the RWM and pushes or deflects the RWM downward. The larger diameter of the flange 12 (relative to the distal dual-needles) also serves as a plug which sealingly engages the border of the opening formed in the RWM, thereby ensuring that all fluid within the RWM is captured and aspirated through the lumen of the needle without any leakage externally of the needle.

In the exemplary embodiment depicted, tips 14a, 14b are formed, e.g. grinded, at angles of ten degrees however alternative angles can be sized as so desired and are considered to be within the scope of the present disclosure. Moreover, the dual-blade tips 14a, 14b can be formed with varying angles along their respective lengths to provide a contoured needle point, if so desired.

Figure 9A:
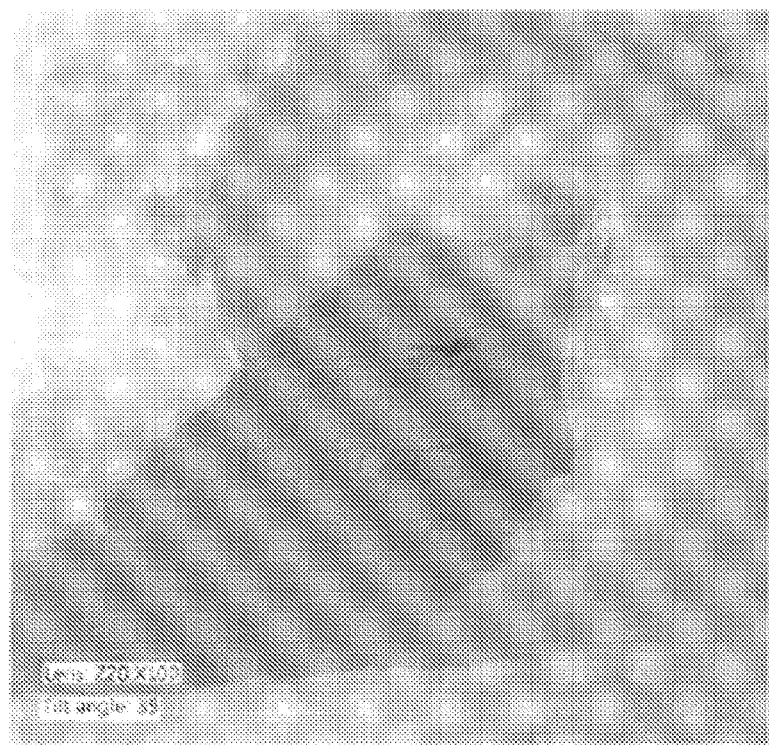
FIG. 9A-B are photographic representations of a perforation of the RWM with one embodiment of an apparatus in accordance with the disclosed subject matter.
Figure 9B:
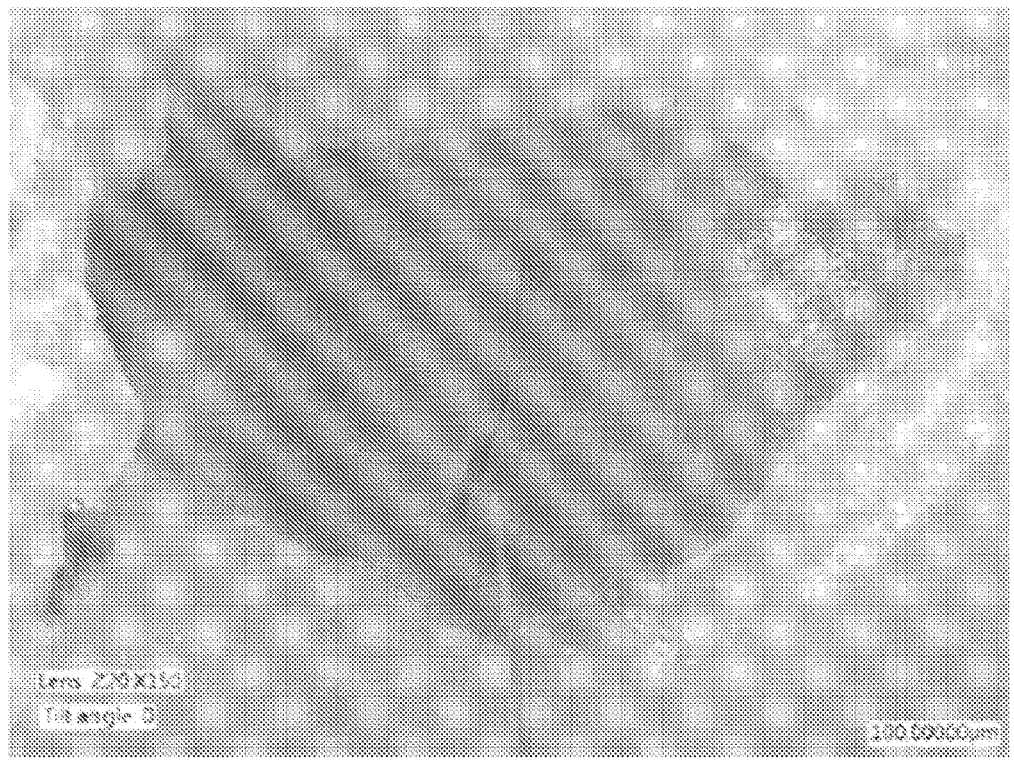

To promote healing after penetration, the dual blade needle and an elliptical cone positioning system are provided such that the flat blade tip 14a,14b cuts the RWM parallel to the direction of the collagen fibers (in the major axis direction of the elliptical membrane). In effect, the cutting operation disclosed herein severs the cross-linking between adjacent fibers rather than severing through the fiber itself. Cutting the RWM in this direction is advantageous in that it reduces the force needed for RWM penetration while also minimizing damage to the membrane's nano-scale collagen architecture, as shown in FIGS. 9A-B. After the apparatus 10 is removed, the scar shape is a line without any removal of the tissue. Furthermore, the surface tension can easily close a micro hole formed in accordance with the present disclosure, facilitating the healing process after the aspiration.

To ensure precise penetration of the RWM without any contact of the needle to inner ear structures such as basilar membrane, a statistical approach can be applied to optimize the length of the blades and apparatus. Further, the apparatus may include a stopper to contact the membrane and control the extent of penetration into the inner ear. To access the RWM through the ear canal, the apparatus is designed to be small and flexible. The size can allow for simultaneous endoscopic visualization, to observe the insertion of an aspirator into the outer and middle ear space.

Figure 10:
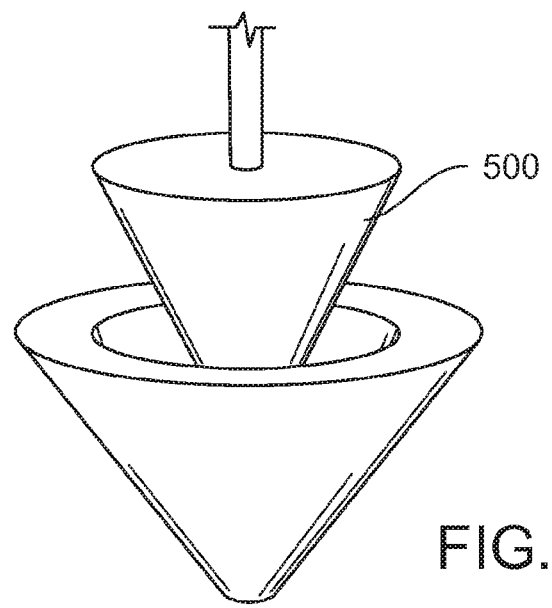
FIG. 10 is a schematic view of an exemplary embodiment of a guide member for use with an aspirating tubular member in accordance with the disclosed subject matter.

Furthermore, to enable precise positioning above the optimal region of the RWM, micro CT scan data of the bony niche can be used to design a guide member 500, e.g., jig (FIG. 10). As the round window niche and RWM faces vertically from the outer ear, visually positioning a needle or apparatus is virtually impossible. The guide jig 500 allows manual positioning by a surgeon, and is optimized to fit the bony niche snugly. The funnel shape of guide member 500 enables guidance toward a targeted spot on the RWM. The guide member 500 can be formed with different size jigs to work with different size niches.

Additionally, or alternatively, sensors and/or an optical scope can be provided to monitor the location and displacement of the needle and RWM during deployment of the needle. In other embodiments an expandable device, e.g. balloon, can be employed as the guide member similarly to the jig described above for precisely guiding the needle to the desired location. Use of a balloon can be particularly advantageous in that it can conform to the unique geometry of the patient, thereby ensuring a proper fit and accurate placement of the needle. In some embodiments, the expandable guide member can be formed from a self-expanding shape-memory material such as nitinol which exhibits martensitic and austenitic properties. Furthermore, the apparatus 10 can be formed with a steerable, or articulating, tip so that the distal tips 14a, 14b can be oriented perpendicularly to the RWM while the remainder of the deployment apparatus may be angled as necessary to position the device within a patient's anatomy.

Figure 11A:
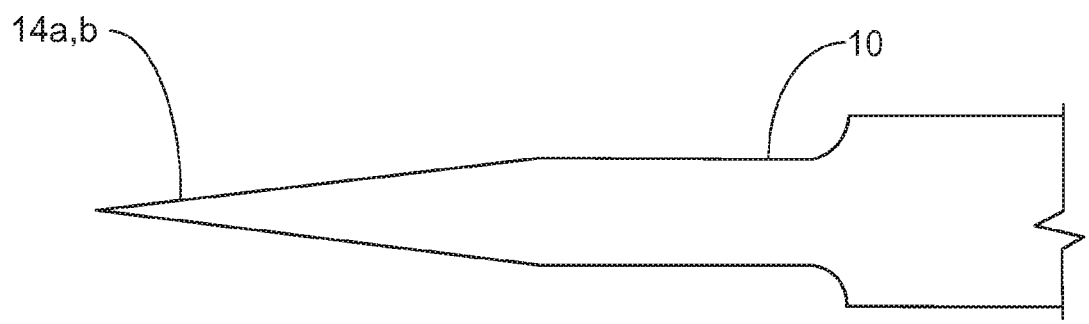
FIGS. 11A-B are schematic views of an aspirating apparatus having dual-wedge blade tip configuration in accordance with one embodiment of the disclosed subject matter.
Figure 11B:
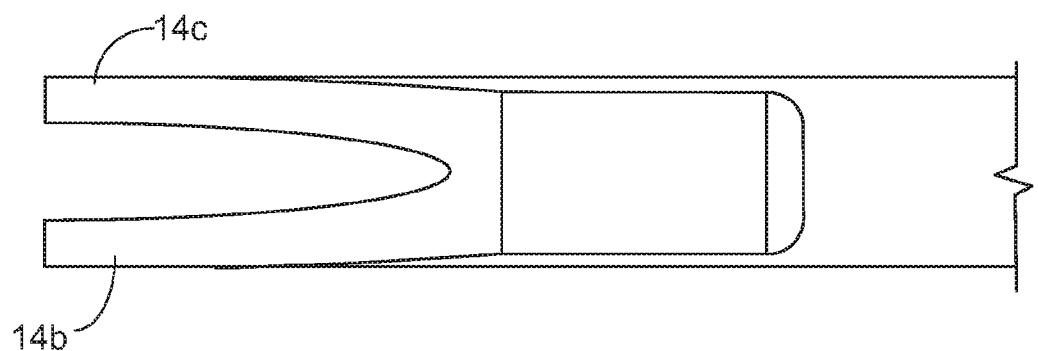

An exemplary illustration of the operation of the dual-tip apparatus 10 into the RWM is depicted in FIGS. 11A-B. The tip of apparatus 10 is oriented at the midpoint of the RWM using any of the guide member features discussed above, e.g., FIG. 9, 500. The needle is located at the midpoint of the RWM as this location will allow the greatest amount of deflection, as shown in FIG. 10B, and thus the greatest amount of perilymph aspiration due to this compression or reduction in volume. As the tips of apparatus 10 penetrate through the RWM (as denoted by the downward arrow) the perilymph fluid is aspirated through the lumen within the lumen of tubular member of apparatus 10 (as denoted by the upward arrow). That is, the RWM can act as a diaphragm to pump the perilymph solution into the lumen as the tip of tubular member is pushed downward or into the RWM. The tubular member of apparatus 10 can be formed with multiple lumens, with certain lumens dedicated for proximal flow (e.g. aspiration) and other lumens dedicated for distal flow (e.g. delivery of therapeutic agents) into the patient. To facilitate the aspiration of the perilymph solution into the needle, the inner surface of the needle lumen can be coated with a lubricant to reduce the capillary forces which can inhibit fluid transfer.

The proximal end of the tubular member can be coupled to a chamber or reservoir for collecting the aspirated fluid. For example, a 10 cm hose can be coupled to the lumen of tubular member in which the hose extends outside the patient so as to be visible to the physician/operator and has a length/volume that equates to a predetermined amount of perilymph fluid. During operation, the operator can confirm that the desired amount of fluid has been aspirated by visually observing that the hose is completely filled. Additionally or alternatively, the collection chamber or reservoir can have graduations that enumerate the amount of fluid contained therein. In some embodiments, the collection chamber or reservoir is removably coupled to the needle and includes a closure, e.g. cap. After aspiration of the perilymph solution the collection chamber can be detached from the needle and closed for transport or subsequent processing.

Figure 12A:
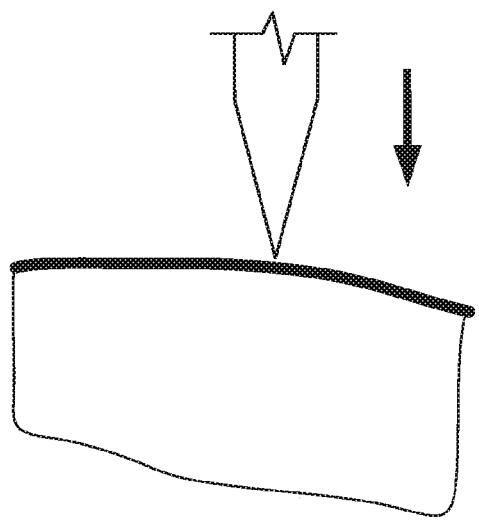
FIGS. 12A-B depict an apparatus in accordance with one embodiment in operation.
Figure 12B:
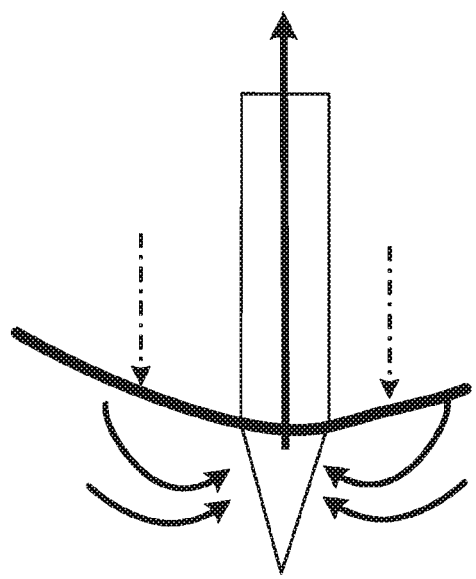

In operation, to detect RWM penetration, an ion sensitive electrode with nano-scale coating of Ag/AgCl is provided that can detect the chloride concentration change that comes from contact with the perilymph. Aspiration, meanwhile, can be assessed with a two-ring system equipped at the end of the catheter that continuously measures the impedance. A change from air to solution during aspiration is readily detected. Aspiration can be accomplished through spontaneous capillary action, assisted by the elastic energy stored within a displaced RWM. Essentially, after penetration the RWM acts as a diaphragm pump using this stored energy to send perilymph solution to the exit with the least fluidic resistant, as described above with respect to FIGS. 12A-B. The pressure necessary for fluid to enter the needle can be analyzed by applying Poiseuille's law:

$$\Delta P = \frac{8 \mu L Q}{\pi r^4}$$

The pressure OP necessary to carry 1 μL of Newtonian fluid, with viscosity of μ=0.001 Pa*s, through a tube of radius r=100 μm, at the volume rate of Q: 0.01 mm³/s=1 μL/100 s, is 25.4 Pa. Conversely, our experimental data of the penetration of the guinea pig RWM as well as computer simulation via ABAQUS predict the displacement of the RWM and the resulting pressure within the inner ear to be up to 100 s of μm and 10 kPa. The RWM will relax and lose elastic energy as the perilymph solution is displaced into the catheter. Even at the moment of aspiration when we detect the sampling of the 1 μL of perilymph, the final pressure is expected to be well above 25.4 Pa. Therefore, the penetration and deformation of the RWM itself will store enough energy to drive perilymph through the catheter system. Additionally, the purity of the perilymph obtained can be assessed, meanwhile, by measuring its potassium or lactate dehydrogenase concentration. Their intracellular contents are high, and could be significantly affected by trauma to surrounding tissues or CSF contamination.

The apparatus 10 described above provides for quick, precise and minimally traumatic sampling of perilymph solution via a round window membrane (RWM) for the diagnosis of inner ear disease. To perforate RWMs minimally traumatically, the mechanical anisotropy was considered. The mechanical properties of the round window membrane (RWM) are thoroughly analyzed and disclosed with the use of nanoindentation, bulge testing, and micro-CT, as disclosed in PCT/US13/75105 and U.S. Provisional Application No. 61/981,458, the entirety of each is hereby incorporated by reference. Additionally, it has been discovered that most human tissues show anisotropy for functional and developmental reasons, with the collagen fibers of RWMs run in the direction of its major axis. The present disclosure also provides a biometrical study using μ-computed tomography to determine the size and variability of the human middle/inner ear anatomy. For instance, the human bony niche provides a narrow entrance (1 mm) to the RWM (2.5~3 mm).

As shown in FIG. 11A, from a side view, the tip 14a and tip 14b, each form one symmetrical wedge to sever a RWM parallel to the underlying collagen fibers so that the incision is linear, rather than round. To allow sampling, a 31 G tubular member can be used for minimal hydrodynamic resistance. The tubular member may be constructed using a wire EDM.

Using a 31 G tubular member, the RWMs of guinea pigs were penetrated in vitro and 1 μL of perilymph was sampled from the cochlea. The solution was analyzed via UV-vis spectroscopy. After sampling, the wedge shaped tips 14a, 14b, left incisions that approximated ovals with minor and major diameter of 143 and 344 μm (n=6). The sampling duration and standard deviation of aspirated volume were a few seconds and 6.8% respectively. The protein concentration of 1.74 mg/mL was confirmed. This demonstrates that the apparatus 10 allows for controllable perforation of RWMs with minimal damage followed by quick and precise aspiration of perilymph.

Accordingly, a hollow tubular apparatus is provided that has the dual objectives of allowing atraumatic insertion into the cochlea through the RWM and subsequent aspiration of a consistent perilymph volume promptly.

EXAMPLES

The apparatus was assembled with a micropipette for sampling perilymph solution of a guinea pig cochlea in vitro. The sampled solution was analyzed via UV-vis spectroscopy to confirm the existence of proteins.

Materials and Methods: Design of a Dual Wedged Needle

To design a needle optimized for the creation of a minimally traumatic hole, the mechanical properties of the RWM was taken into account. Unlike the name may suggest, the RWM has an oval shape in a plan view and is woven with nano-meter scale collagen fibers. These fibers run parallel to the major axis of the oval resulting in the property called anisotropy. This anisotropy is the mechanical property describing that the RWM is stronger in the major axis orientation than in the minor axis. Consequently, a perforation with a regular round needle tends to be an asymmetric oval shape. To take advantage of this anisotropy, needle of the present disclosure makes a linear incision along the direction of the collagen fibers to reduce the energy of perforation and consequently minimize the trauma to facilitate subsequent healing process. FIG. 1 shows the design of the dual wedge needle. The standard anatomical terms of location are used to define the direction. In the frontal plane view, the needle has a tip with two blades. In the longitudinal plane view, these two blades are aligned in the center of the needle making the shape of one symmetrical wedge. These two linear blades are intended to sever the collagen fibers parallel to them and open the linear incision by the wedge to allow for making a hole with minimum size necessary for the aspiration of the perilymph solution.

To realize prompt aspiration of perilymph solution at negligible small pressure, fluid dynamics was considered and the dimension of the needle was determined as follows. Smaller the size of the needle diameter, less atraumatic to the RWM. However, the time necessary for the aspiration increases as the inner bore diameter become smaller. When a 31 gauge needle is used for aspiration, the pressure necessary for fluid to enter the needle can be estimated by applying Poiseuille's law, given in Equation 1, where the pressure AP necessary to carry 1 µL of Newtonian fluid, with viscosity of µ=0.001 Pa*s, through a tube of radius r=100 µm, at the volume rate of Q: 0.01 mm3/s=1 µL/100 s, is 25.4 Pa (=2.5 mmH2O). This dimension will provide negligible hydrodynamic resistance for the aspiration of perilymph solution.

$$\Delta P = (8\mu L Q)/(\pi r^4)$$ Equation 1

Figure 13:
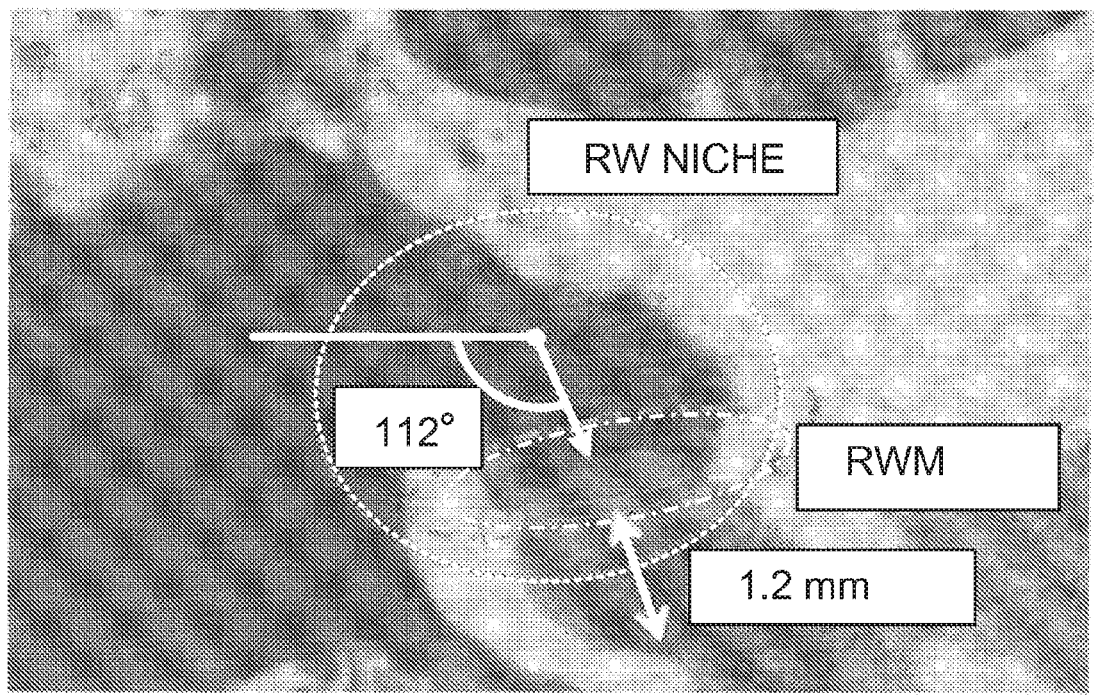
FIG. 13 is a micro CT scan image showing a round window niche and a round window membrane of a human cadaveric temporal bone

The angle of the wedge was minimized for the small force penetration to the extent in which the tip does not make any contact to the inner ear wall or basilar membrane. FIG. 13 shows a micro CT scan image (SkyScan 1172; Bruker microCT, Belgium) of a human cadaveric ear. A fresh temporal bone was purchased (Science Care, Phoenix, Ariz.) and drilled to optimize the resolution of the scan. The distance between the RWM and the basilar membrane was estimated to be 1.2 mm. Therefore, the length of the wedge was determined as 0.6 mm such that the wedge has enough sharpness to penetrate a RWM.

In some embodiments, a tubular member according to the present disclosure meets the following anatomical criteria: Length limit of 1.2 mm to prevent inner ear damage; A curved aspiration canal system: a bendable/flexible tube. In some embodiments, a needle according to the present disclosure meets the following mechanical property criteria: Anisotropic strength of RWMs: penetration of a RWM in a weaker direction; Minimal size of an incision to minimize the damage to a RWM. In some embodiments, a tubular member meets the following fluid dynamic criteria: A few to 60 seconds aspiration—negligible fluidic resistance. In some embodiments, a tubular member according to the present disclosure meets the following anatomical criteria: Wedge length 0.6 mm; Stopper at 1.0 mm from the tip; A flexible gauge 30 polyimide tube. In some embodiments, a tubular member according to the present disclosure meets the following mechanical property criteria: Sharp linear wedge shape (tip curvature 2 µm); Size of the needle: 0.14×0.256 mm. In some embodiments, a tubular member according to the present disclosure meets the following fluid dynamic criteria: 31 gauge needle: 256/128 µm outer/inner diameter.

As in the embodiment of FIG. 1, the aspirating tubular member 10 can include a stopper or a physical mark to determine when to stop insertion of the tubular member in the ear. In the longitudinal plane (FIG. 11B), proximate the wedge portion of the tubular member, a 0.4 mm length sliding stopper is provided. This "slide and stop" region of the tubular member provides a stop point of penetration and start point for sampling of fluid. This region can be larger than the inner diameter and thinner than the outer diameter of the tubular member such that the perforation in the RWM becomes narrower.

Production and Evaluation

Wire electro discharge machining R40 (EDM) (Mitsubishi, Japan) was used to fabricate the dual wedge needles. A medical grade stainless steel 31 gauge hypodermic needle was purchased from Small Parts (Logansport, Ind.). The needle was fixed using a specialized jig aligned precisely along the 3 dimensional coordinate system of the EDM. A cutting path consisting of one rough cut followed by 4 skim cuts was determined to define the dual wedge needle from the longitudinal plane view. The 4 skim cuts were required to improve the precision and minimize surface roughness.

The roughness and sharpness of the dual wedge needle was evaluated with 3-D Optical Surface profilers NewView 7400 (Zygo, CT). The surface topography was obtained first from frontal plane and transverse plane views of the dual wedge needle. Using the topographical data from the frontal plane view, the root mean square roughness of the cutting surface was calculated using MetroPro (Zygo, CT). The surface roughness of a hypodermic needle was used as a control. The sharpness was quantified as the curvature radius of the wedge tip. In the transverse plane view data in which the needle tip was looked down, the 3D shape of the edge of the two linear blades was obtained such that the curvature of the whole length of the wedge tips could be calculated. Using MATLAB (Mathwork, MA), the mean cross section of the wedge shape along the whole length was calculated. A quadratic curve fit was performed on the cross section and the inverse of the second derivative of the function was used as a curvature radius.

Sampling Precision Confirmation.

The precision of the sampling method was confirmed by measuring the weight of the sampled solution for 20 times using an analytical scale PI-214A (DENVER, N.Y.) at the precision of 0.1 mg. The prototyped dual wedge needle was glued to a 30 G polyimide tube (Small parts, IN) that was also glued to a 10 µL micropipette tip (Eppendorf, Germany) using 2 ton epoxy (Devcon, MA). Using an Eppendorf micropipette, 1.0 µL of a saline solution was sampled through the wedge needle and ejected to a microcentrifuge tube (Cole-Parmer, IL). Since the density of a saline water is 1.0046 g/mL, this scale provides 0.1 µL precision in volume measurement. Average ejection weight was 0.995 mg with the standard deviation of 7.6%.

In Vitro Demonstration with a Guinea Pig Cochlea

Guinea pig *cochleae* were used for demonstration. The size of the RWM and the volume of the cochlea of a guinea pigs are much smaller than those of humans. Therefore, the demonstration in this smaller size will provide a strong case for concluding that a larger sized human RWM will be less traumatic than the results in this study.

Guinea pigs with no history of middle ear disease were euthanized under pentobarbital anesthesia according to IACUC at Columbia University. Within 10 minutes after euthanization, the both side of *cochleae* were harvested. The cochlea bones were trimmed by drilling to remove the bone hanging over the RWMs and to ensure the passage of the needle yet with minimal damage to the canals of the inner ear. The cochlea bones were fixed on a petri dish filled with saline solution providing moisture. And, the dual blade needle was lowered slowly with the control of micromanipulator. The penetration of the RWM was confirmed with a binocular microscope. The needle was lowered until the wedge was lowered below the membrane completely. The micropipette attached to the dual wedge needle was used to aspirate 1 µL of perilymph solution. After the aspiration, the dual wedge needle was retracted. The aspirated perilymph solution was ejected to 39 µL of saline solution in a microcentrifuge tube.

Immediately after the sampling experiment, the inner ears were fixed in 10% neutral buffered formaldehyde solution overnight. The detail of dehydration process for scanning electron microscopy was described previously. Briefly, after dehydration using ethanol, critical point drying was performed with hexamethyldisiloxane. After coating of gold, scanning electron microscopy was performed to determine the shape and size of the incision.

UV-Vis Absorbance Spectroscopy of Sampled Perilymph Solution for Protein Analysis To demonstrate the analysis of protein in the perilymph and confirm the success of sampling biological solution, the sampled perilymph solution was analyzed via UV-Vis absorbance spectroscopy using a plate reader Synergy 4 (Biotek®, VT). The solution was kept temporarily in a microcentrifuge tube and mixed with a vortex mixer. The 20 µL solution was transferred to a Corning® UV plate flat bottom for 96 wells and additional 20 µL saline solution was poured. The plate reader procedure was 30 second shake followed by absorption spectroscopy of UV and visible light (200~800 nm). The concentration of protein mixtures was roughly estimated by Equation 2 where X: the concentration (mg/mL), A: absorbance, and L: path length (cm). Path length of the specimen was calculated as 0.63 mm by dividing the volume of 40 µL by the surface area of the bottom from the diameter of 6.35 mm. The ratio of the dilution was taken into account.

$$X = A/L \quad \text{Equation 2}$$

Results

Figure 14A:
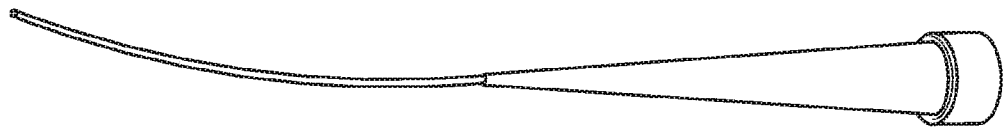
FIG. 14A-C are perspective views of a prototype in accordance with an aspirating apparatus in accordance with an embodiment of the disclosed subject matter.
Figure 14B:
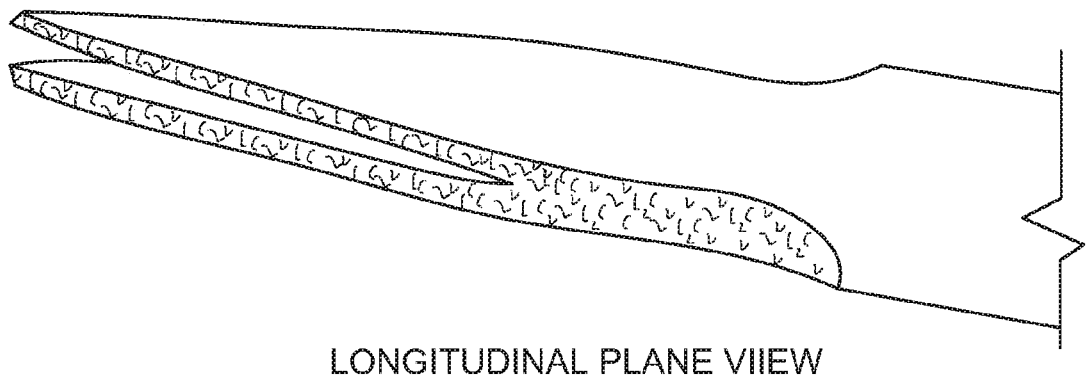
Figure 14C:
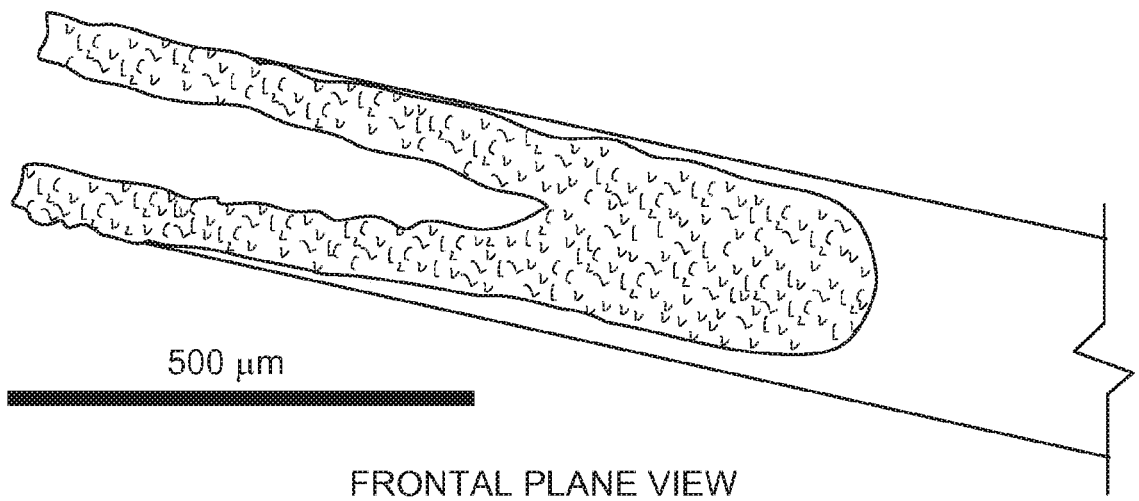

FIG. 14 shows prototype dual wedge needle used in the examples described above. FIG. 14 shows an assembled apparatus having an adapted needle for sampling perilymph using a micro-pipette at the proximal end of the apparatus for suction. A polyimide tubular member disposed between the micro-pipette and adapted needle was used for flexibility and tight fit with the dual wedge needle. In this study, an oversize stainless steel tube was put on over the polyimide tube to stabilize the needle during the penetration of the guinea pig RWM. FIGS. 14B and 14C show detailed views of the tip of a needle according to the present disclosure.

Figure 15:
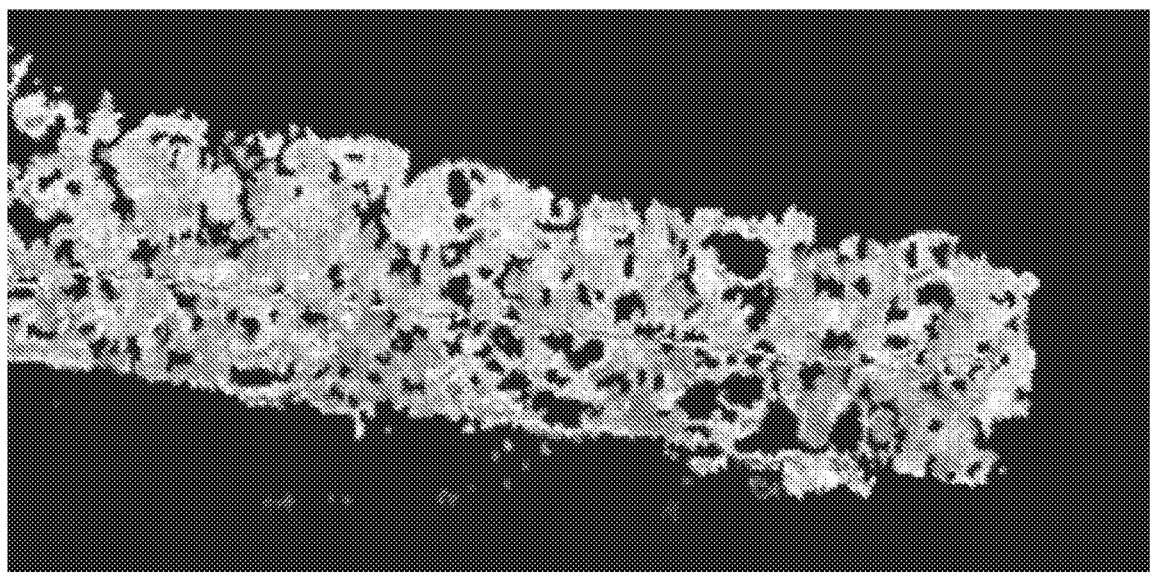
FIG. 15 shows the topography of the one blade of the dual wedge needle captured from the frontal view plane.
Figure 16:
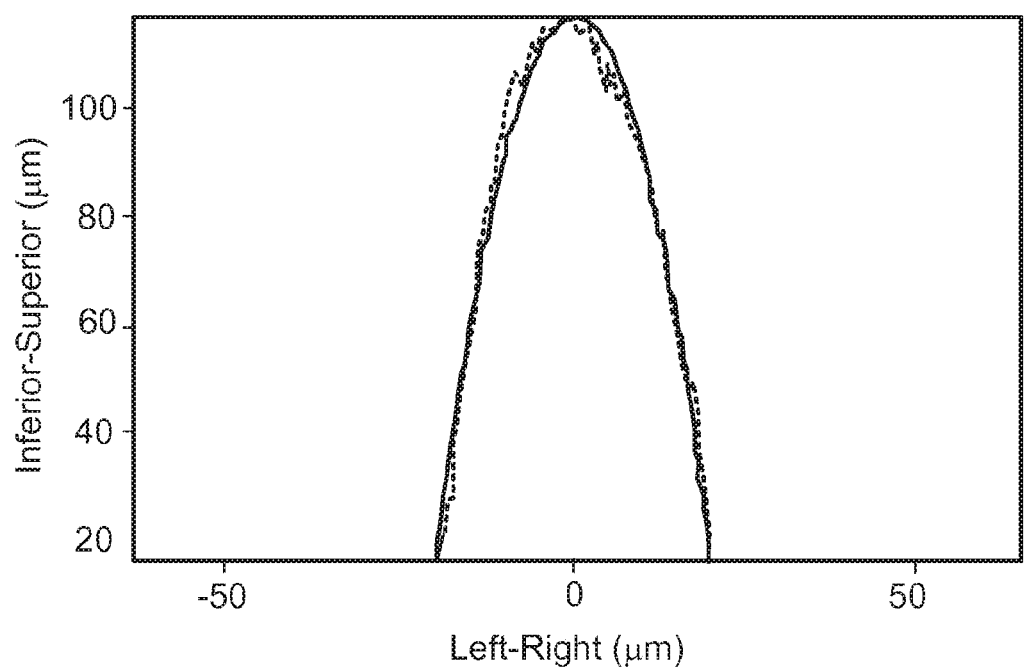
FIG. 16 depicts the average cross section of a dual wedge needle in dotted line. The quadratic fit curve in broken dashed line.

FIG. 15 shows the topography of the one blade of the dual wedge needle captured from the frontal view plane. The surface roughness is 3.66 µm in root mean square. That of hypodermic needle is 3.15 µm (topographical data not shown). FIG. 16 shows the average profile of the cross section of the tip of the wedge needle in longitudinal plane views in the green line. The blue broken line is the quadratic fit curve. The curvature radius of the tip was 4.5 µm.

Linear Incision in the Guinea Pig RWM

Figure 17A:
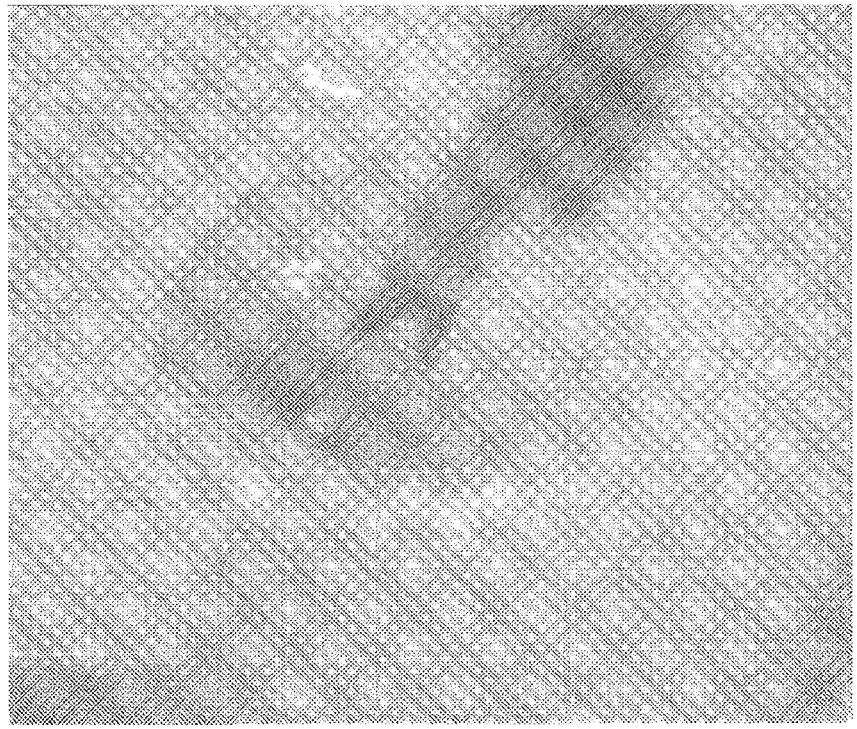
FIG. 17A is an optical micrograph of a RWM of a guinea pig before the penetration by an apparatus of the disclosed subject matter.
Figure 17B:
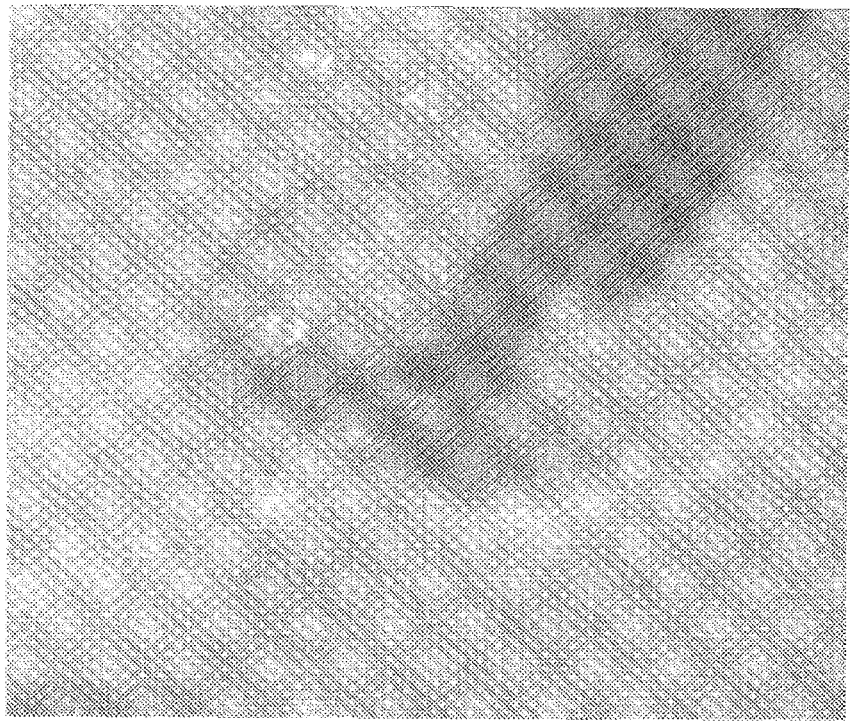
FIG. 17B is an optical micrograph after the penetration of a RWM of a guinea pig by an apparatus having a stopper in accordance with one embodiment of the described subject matter.
Figure 18A:
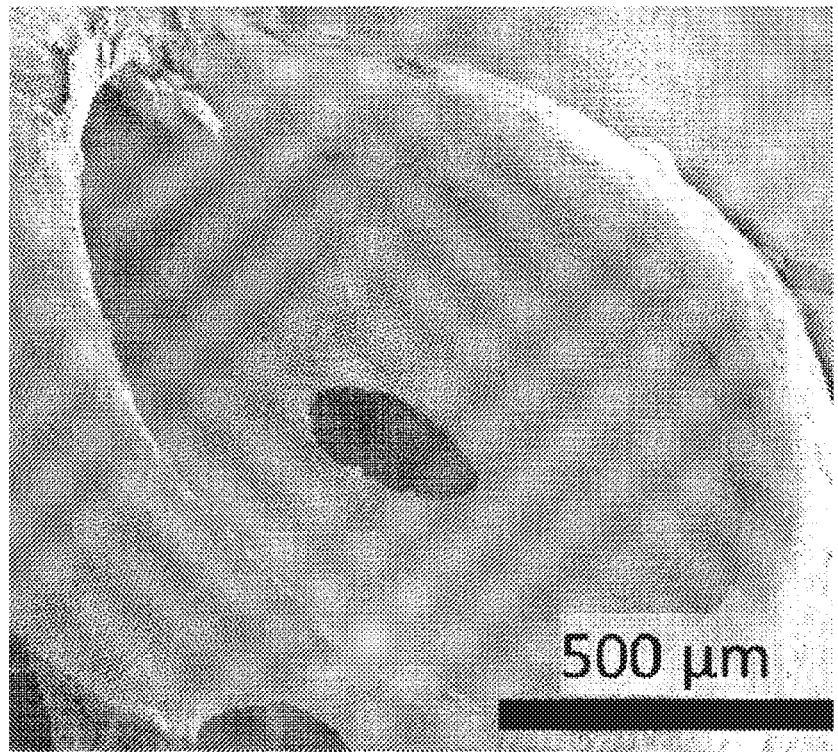
FIG. 18A-B are scanning electron micrograph of a guinea pig RWM after sampling of perilymph solution.
Figure 18B:
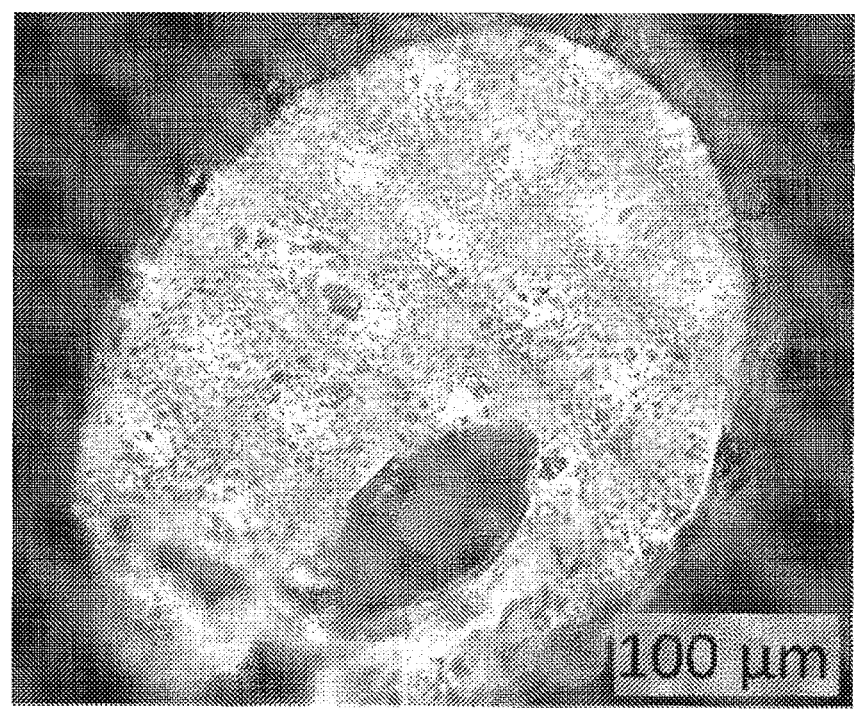
Figure 19:
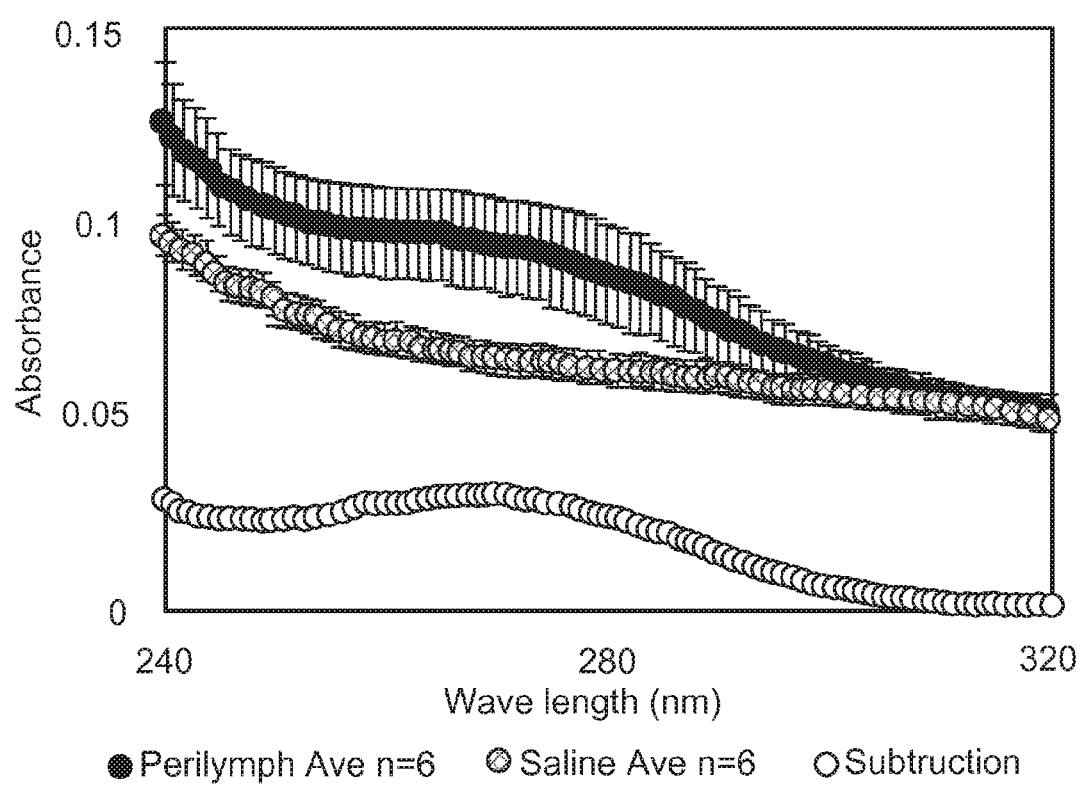
FIG. 19 is UV-Vis spectroscopy of sampled perilymph (blue) and saline solution (red).
Figure 20A:
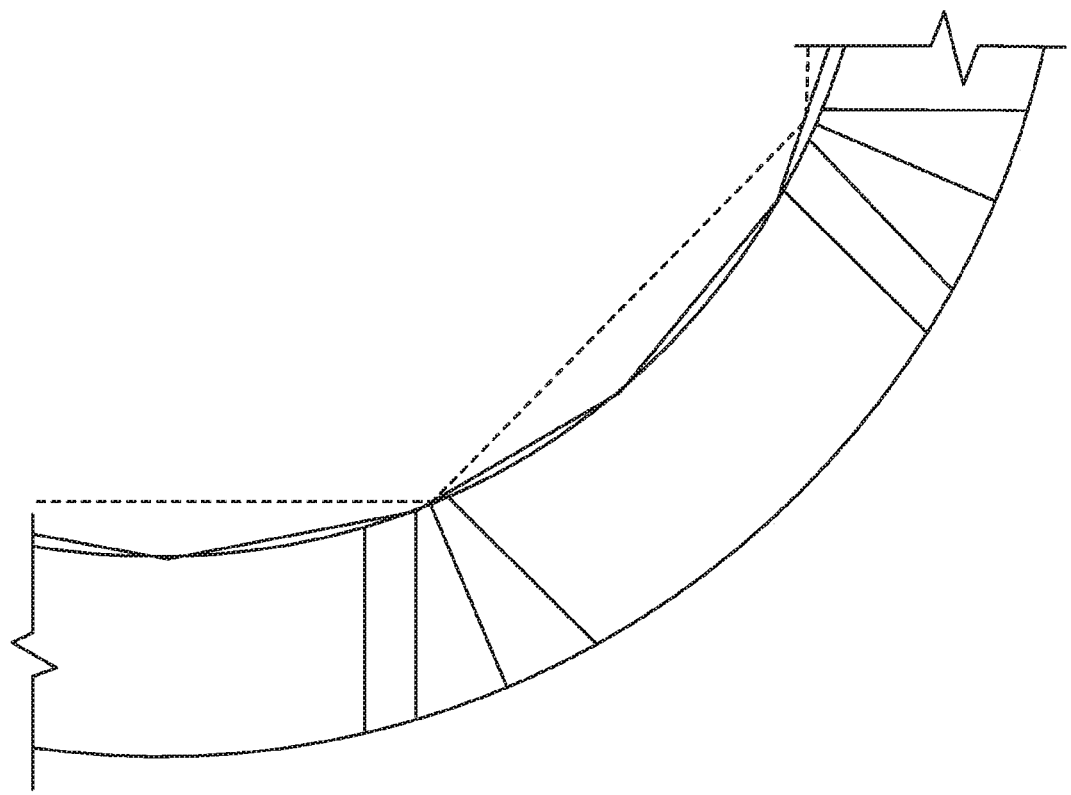
FIG. 20A-B are top views of the tubular member distal end illustrating the inner and outer diameters of the tubular member in accordance with an exemplary embodiment of the tubular member.
Figure 20B:
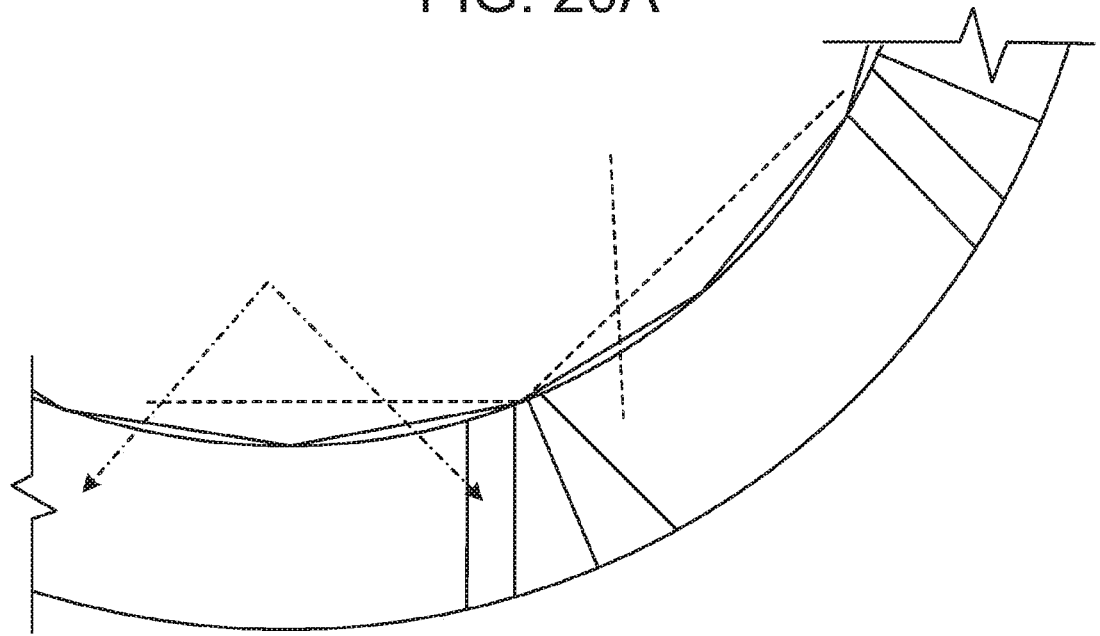

FIG. 17A is an optical micrograph captured through an eyepiece of a binocular microscope after the penetration of the RWM. The moment of initial penetration was easily confirmed when the RWM popped up by the spring-back-action of the RWM. Further penetration was terminated visually at the stopper of the needle. FIG. 17A shows the electron micrograph of the perforated RWMs of guinea pigs. Each hole had a flattened oval shape. All of the RWM kept the integrity intact except for the oval hole. The average major and minor axis diameter were 344 and 143 µm with the standard deviation of 37.9 and 26.5 µm (11 and 19%). Pearson's r between the major and minor diameter was 0.4. These two types of values suggest that the size of hole varies with small geometrical similarity. Aspect ratio was 0.416 with standard deviation of 6.7%. The t-value for a 95% confidence was 0.013 from a comparison of the groups of major diameter multiplied by 0.4 and the minor diameter. FIG. 17B shows a comparable optical micrograph of a RWM with a hole penetrated manually by an insect pin with the diameter of 100 µm. Typically, the hole expands as great as 5 times in both major and minor axes when a round needle penetrates the RWM of a guinea pig.

The Concentration of Protein in the Perilymph Incision

FIG. 16 shows the absorbance spectroscopy of the sampled perilymph solution, saline solution and the subtraction curve of the two curves in blue, red and green in the wavelength range of 240 to 320 nm. From the t-value of the two curves, the difference was clear suggesting the presence of the protein. The subtraction curve showed peaks of 0.39 and 0.030 at 205 and 270 nm. The absorbance at 280 nm was 0.027. The protein concentration was estimated to be 1.74 mg/mL.

Design and Production of the Needle

The prototyped dual wedge needle of the present disclosure is designed for smooth penetration of a guinea pig RWM, precise and quick sampling of perilymph, and control of the incision to minimize the damage. The production method using wire EDM is adequate for the design. A more conservative manufacturing process of grinding used to manufacture hypodermic needles can be applied to reproduce the present needle for cost, scalability, and compatibility for clinical use.

The flexible tubular member can be useful for embodiments in which the sampling tube needs a curved canal. In this embodiment, the tubular member can be formed from material with suitable flexibility such as polyimide and other polymers with similar durometer. When a needle was inserted through an external ear canal, the RWM does not face perpendicular to the angle of these approaches. Thus, some embodiment have a curved shape close to the tip in order to approach and penetrate the RWM vertically against it. Like tools such as a Rosen needle that has the curve at the tip, this flexible polyimide tube enables embedding the canal system for aspiration.

Precise and Quick Sampling

The 31 gauge needle used in some embodiments has small enough fluidic resistivity to aspirate the 1 µm of perilymph solution within a few seconds with great accuracy. This fluidic resistivity provides enough room to further improve the atraumacity of perilymph sampling. In addition to the precise control over the volume of the perilymph sample, minimizing intrascalar pressure is also critical for atraumacity of the inner ear structure. Some complication that can be caused by intracochlear pressure change are suggested in the cases of cochlear implantation, Meniere's disease or barotrauma experienced by divers. While minimizing the volume of perilymph solution removed alone will reduce the risk of physical damage caused by the pressure, slowing down the aspiration will likely minimize the pressure and the risk as well.

The volume of the human scala tympani is on the order of a 44 µL. Thus, 1.0 of perilymph removal is 2.2% of the entire volume. The scala tympani is connected to the entire inner ear through helicotrema and the partially sealed cochlea aqueduct next to the RWM communicates moderately with cerebrospinal fluid. The fluidic conductance through these routes is limited and the dynamic pressure grows proportionally to the fluidic resistance and the speed of fluidic flow. Although, the rate of the perilymph flow rate in a healthy human individual is not yet known, the flow rate of a guinea pig is 0.001 to 1 µL/min. Therefore, some embodiment have a pressure, flow rate, and volume control system to slow down the aspiration speed from 0.3 down to 0.01 µL/sec. Further, this aspiration method may be validated with an intrascalar pressure sensing experiment. Lastly, these systematic approach will also evaluate possible contamination from the cerebral spinal fluid to ensure the high quality sampling of perilymph solution.

Atraumatic Sampling: Force Required to Penetrate, Shape of the Hole

Larger holes seen in a RWM than the holes seen in this study are known to heal spontaneously within a few days without significant damage to hearing. The results herein demonstrate that the needle of the present disclosure is capable of leaving incisions of an oval shape with the minor axis diameter smaller than the diameter of a 31 gauge needle. A healthy RWM used in this study is under pretension and, without proper care, penetration can rip the hole causing catastrophic rupture and resulting in complete loss of the RWM. The consistent size and shape of the perforation demonstrated that the sampling via the prototyped needle minimized such a risk. The human RWM has much larger size than a guinea pig. The penetrating a human RWM using the needle showed better chances of minimizing the trauma due to structurally stronger human RWM than a guinea pig RWM.

Molecular Analysis of the Sampled Perilymph Solution

The sampled fluid was biological solution as shown by confirming the presence of proteins via absorbance spectroscopy. Although the concentration estimation was rough, the value of 1.74 mg/mL is close to the literature values of 1.50 and 2.757±0.238 mg/mL. The protein constituents of the sampled solution can be analyzed and identified via liquid chromatography—mass spectrometry. In guinea pig model, by independently identifying the protein constituents of perilymph from the apex of the cochlea and CSF from spinal cord, we can quantify the proportion of perilymph and CSF.

The tubular member having a dual wedge tip can be fabricated using a wire EDM. The tubular member can be fabricated with high quality, i.e. excellent sharpness at the tip as well as smooth surface. A precise aspiration can be provided in conjunction with a micropipette, or other device causing an aspirating force to suction of vacuum the fluid from the inner ear. Perilymph can be sampled from a cochlea while leaving a controlled oval perforation.

The apparatuses described herein can be used for in-office diagnosis via sampling of perilymph solution. An effective sampling method of the perilymph through the RWM will greatly ameliorate the current proteomic analysis of the contestants for diagnosis and facilitate more directed approaches to treatment. Moreover, medications can be specifically targeted to the faulty outer hair cells typically associated with SSNHL, while leaving other parts of the inner ear undamaged. The growth of new hair cells in mammals can be induced through the inhibition of the Notch signaling pathway. Once the etiology and pathophysiology of a given patient's presentation is understood, the specific affinity properties of carrier materials may be used to target tissues, cell-specific receptors/promoters, or the restricted biochemical reactiveness of proteins in cells. This provides the foundation for molecular therapy for inner ear disorders. An atraumatic, precise approach to perilymph sampling provides the basis for effective fluid analysis through various techniques, including liquid chromatography—tandem mass-spectrometry (LC-MS/MS). Such analysis allows the amount of data describing gene expression and proteomics to rapidly grow.

However, prior tools used to sample the perilymph solution for diagnosis have not been optimized for the patients to outweigh the benefit of perilymph sampling over risk associated to the operation. During major surgeries for cochlear implantation or tumor resection, previous studies for perilymph collection was performed intra-operatively using glass capillary. A diagnosis must be performed without any major surgery. The use of a fragile glass capillary has the risk of failure of the tool as well as the extended duration of sampling due to the slow process of the capillary action. In animal studies, methods of perilymph sampling have utilized the creation of a basal or apical cochleostomy, requiring disruptive surgical drilling of the cochlear wall and putting the patient at risk for hearing loss. Alternatively, the round window membrane (RWM), is the membranous entrance into the perilymph-filled scalae of the cochlea, provides a promising portal for fluid aspiration that can heal spontaneously. As a matter of fact, there is no other route than through the ear canal, middle ear and the RWM where a physician can have access to the inner ear space without causing permanent damage to a patient. The tools of the present disclosure that facilitate to aspirate the perilymph solution during exploratory tympanostomy tremendously reduce the risk for a patient and improve the quality of diagnosis based on molecules in the inner ear fluid.

While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments. In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An apparatus for penetrating a membrane of an inner ear of a patient comprising:
   a hollow tubular member with an outer diameter of about 0.8 to about 1.1 mm having a proximal portion and a distal portion and a length therebetween,
   wherein the distal portion includes a plurality of alternating apices and valleys to define a plurality of serrated blades, wherein each apex includes a pointed tip at the distalmost end and a tip sharpness with a tip radius of curvature of 2 µm or 4.5 µm and a trailing edge extending proximally from the tip of the apex to the valley and the valleys include an arcuate edged surface disposed between pairs of apices.

2. The apparatus of claim 1, wherein the apparatus has two serrated blades.

3. The apparatus of claim 2, wherein the two serrated blades each have a wedge configuration.

4. The apparatus of claim 1, wherein the apparatus has eight serrated blades.

5. The apparatus of claim 1, wherein the tubular member is a metallic needle.

6. The apparatus of claim 1, wherein the pointed tips of the apices have a polyhedral configuration.

7. The apparatus of claim 6, wherein the polyhedral configuration has multiple faces extending proximally from tips of the apices.

8. The apparatus of claim 7, wherein the intersection of the multiple faces form a cutting edge.

9. The apparatus of claim 6, wherein a surface of at least some apices form an angle of about 15 degrees with a longitudinal axis of the tubular member.

10. The apparatus of claim 1, wherein the tubular member has an outer diameter of about 1 mm.

11. The apparatus of claim 10, wherein the tubular member has an inner diameter of about 0.6 mm to about 0.8 mm.

12. The apparatus of claim 1, wherein the distal portion of the tubular member has a length of about 2 mm.

13. The apparatus of claim 1, wherein the tubular member further includes a stopper disposed proximal to the distal portion of the tubular member.

14. The apparatus of claim 1, wherein the proximal end of the tubular member is configured to engage a handle.

15. An apparatus for penetrating a thin membrane of an inner ear of a patient comprising:
a tubular member having a proximal portion and a distal portion and a lumen therebetween,
a plurality of serrated blades at the distal end of the tubular member, the plurality of serrated blades defined by alternating apices and valleys, wherein the apices and the valleys define a continuous ridge, the continuous ridge defining a cutting edge, wherein the tip has a radius of curvature, and further wherein the tip radius of curvature is 2 μm.

16. The apparatus of claim 15, wherein the tubular member includes a stopper coaxially disposed about the tubular member.

17. The apparatus of claim 15, wherein the plurality of alternating apices and valleys define two spaced apart serrated blades.

18. The apparatus of claim 15, wherein the valleys include an arcuate edged surface disposed between pairs of apices.

19. The apparatus of claim 15, wherein the plurality of serrated blades consists of eight serrated blades.

20. The apparatus of claim 15, wherein the tubular member includes a bevel angle of 15 degrees formed by the apices and a longitudinal length of the tubular member.

21. The apparatus of claim 15, wherein the tubular member has an outer diameter of about 0.8 to 1.1 mm.

22. An apparatus for penetrating a thin membrane of an inner ear of a patient comprising:
a tubular member having a proximal portion and a distal portion and a lumen therebetween, a plurality of serrated blades at the distal end of the tubular member, the plurality of serrated blades defined by alternating apices and valleys, wherein the apices and the valleys define a continuous ridge, the continuous ridge defining a cutting edge, wherein the tip has a radius of curvature, and further wherein the radius of curvature is 4.5 μm.

23. An apparatus for penetrating a membrane of an inner ear of a patient comprising:
a tubular member having a proximal portion and a distal portion and a lumen therebetween, and
a plurality of serrated blades at the distal end of the tubular member, the plurality of serrated blades defined by alternating apices and valleys, wherein each apex has a pointed tip and a trailing edge extends proximally from the pointed tip to the valley to form a cutting blade, and further wherein the tubular member includes a bevel angle formed by the apices and the tubular member, wherein the tip has a radius of curvature, and further wherein the tip radius of curvature is 2 μm.

* * * * *